United States Patent
Ackerman et al.

(10) Patent No.: US 11,191,435 B2
(45) Date of Patent: *Dec. 7, 2021

(54) PROBE WITH OPTOACOUSTIC ISOLATOR

(71) Applicant: Seno Medical Instruments, Inc., San Antonio, TX (US)

(72) Inventors: William Ackerman, Somerdale, NJ (US); Donald G. Herzog, Collingswood, NJ (US); Justin Casas, San Antonio, TX (US)

(73) Assignee: SENO MEDICAL INSTRUMENTS, INC., San Antonio, TX (US)

( * ) Notice: Subject to any disclaimer, the term of this patent is extended or adjusted under 35 U.S.C. 154(b) by 517 days.

This patent is subject to a terminal disclaimer.

(21) Appl. No.: 13/746,905

(22) Filed: Jan. 22, 2013

(65) Prior Publication Data

US 2014/0206978 A1 Jul. 24, 2014

(51) Int. Cl.
*A61B 5/00* (2006.01)
*G01N 21/17* (2006.01)
*A61B 8/00* (2006.01)

(52) U.S. Cl.
CPC .......... *A61B 5/0095* (2013.01); *A61B 8/4444* (2013.01); *G01N 21/1702* (2013.01);
(Continued)

(58) Field of Classification Search
CPC . A61B 5/0095; A61B 8/4281; A61B 5/14542; A61B 5/0073; A61B 2560/0223;
(Continued)

(56) References Cited

U.S. PATENT DOCUMENTS

| | | | |
|---|---|---|---|
| 4,083,224 A * | 4/1978 | Gayst | G01N 25/68 374/19 |
| 4,258,977 A | 3/1981 | Lukas et al. | |

(Continued)

FOREIGN PATENT DOCUMENTS

| | | |
|---|---|---|
| EP | 0282234 A1 | 9/1988 |
| EP | 1210910 A1 | 6/2002 |

(Continued)

OTHER PUBLICATIONS

Beard, Paul. "Biomedical photoacoustic imaging". Interface Focus rsfs20110028; published ahead of print Jun. 21, 2011, doi:10.1098/rsfs.2011.0028 2042-8901.*

(Continued)

*Primary Examiner* — Amanda Lauritzen Moher
(74) *Attorney, Agent, or Firm* — The Small Patent Law Group LLC; Josef L. Hoffmann

(57) ABSTRACT

An optoacoustic probe including an ultrasound transducer array, an acoustic lens and a light path separated from the transducer array by an isolator to mitigate light energy from the light path from reaching the transducer array. The isolator being formed from a mixture including a flexible carrier, a coloring and between 10% and 80% by volume micro-bubbles. The isolator mixture being adapted to both absorb light energy and the optoacoustic response to light energy. In an embodiment, an optoacoustic probe also comprises an optical window and/or a diffuser, and the isolator also separating the transducer array from these components.

21 Claims, 10 Drawing Sheets

(52) U.S. Cl.
CPC ..... *A61B 8/4281* (2013.01); *A61B 2562/0204* (2013.01); *A61B 2562/0233* (2013.01); *A61B 2562/16* (2013.01)

(58) Field of Classification Search
CPC ...... A61B 2560/0276; A61B 2560/028; A61B 2560/0431; A61B 2562/0204; A61B 2562/0233; A61B 2562/16; A61B 5/065; A61B 5/4312
See application file for complete search history.

(56) References Cited

U.S. PATENT DOCUMENTS

| | | |
|---|---|---|
| 4,267,732 A | 5/1981 | Quate |
| 4,651,850 A | 3/1987 | Matsuo |
| 5,062,715 A | 11/1991 | Nakata et al. |
| 5,148,233 A | 9/1992 | Imamura et al. |
| 5,293,873 A | 3/1994 | Fang |
| 5,341,204 A | 8/1994 | Grant et al. |
| 5,348,002 A | 9/1994 | Caro |
| 5,460,182 A | 10/1995 | Goodman et al. |
| 5,504,281 A * | 4/1996 | Whitney ............... H04R 1/02 181/286 |
| 5,713,356 A | 2/1998 | Kruger |
| 5,800,350 A | 9/1998 | Coppleson et al. |
| 5,840,023 A | 11/1998 | Oraevsky et al. |
| 5,935,288 A | 8/1999 | DiGiovanni et al. |
| 5,946,081 A | 8/1999 | Lai et al. |
| 5,977,538 A | 11/1999 | Unger et al. |
| 6,117,080 A | 9/2000 | Schwartz |
| 6,126,605 A | 10/2000 | Washburn et al. |
| 6,216,025 B1 | 4/2001 | Kruger |
| 6,249,751 B1 | 6/2001 | Asaba et al. |
| 6,263,094 B1 | 7/2001 | Rosich et al. |
| 6,498,942 B1 | 12/2002 | Esenaliev et al. |
| 6,617,559 B1 | 9/2003 | Emery et al. |
| 6,650,928 B1 | 11/2003 | Gailly et al. |
| 6,656,119 B2 | 12/2003 | Sasaki et al. |
| 6,716,172 B1 | 4/2004 | Kerby et al. |
| 6,751,490 B2 | 6/2004 | Esenaliev et al. |
| 6,904,306 B1 | 6/2005 | Wu et al. |
| 6,979,292 B2 | 12/2005 | Kanayama et al. |
| 7,327,896 B1 | 2/2008 | Singh et al. |
| 7,515,676 B2 | 4/2009 | Zamyatin |
| 7,517,157 B1 | 4/2009 | McNiece et al. |
| 7,675,013 B2 | 3/2010 | Kobayashi et al. |
| 7,729,735 B1 | 6/2010 | Burchman |
| 7,741,900 B1 | 6/2010 | Li |
| 7,972,272 B2 | 7/2011 | Munce et al. |
| 8,016,419 B2 | 9/2011 | Zhang et al. |
| 8,025,406 B2 | 9/2011 | Zhang et al. |
| 8,109,981 B2 | 2/2012 | Gertner et al. |
| 8,144,327 B2 | 3/2012 | Nakajima et al. |
| 8,214,010 B2 | 7/2012 | Courtney et al. |
| 8,298,144 B2 | 10/2012 | Burcher |
| 8,300,224 B2 | 10/2012 | Nakajima et al. |
| 8,327,973 B2 | 12/2012 | Parish et al. |
| 8,353,830 B2 | 1/2013 | Kanayama et al. |
| 8,353,833 B2 | 1/2013 | Dogra et al. |
| 8,460,195 B2 | 6/2013 | Courtney et al. |
| 8,480,584 B2 | 7/2013 | Kanayama et al. |
| 8,686,335 B2 | 4/2014 | Schmid et al. |
| 8,712,506 B2 | 4/2014 | Courtney et al. |
| 8,784,318 B1 | 7/2014 | Napolitano et al. |
| 8,823,928 B2 | 9/2014 | Herzog et al. |
| 8,870,770 B2 | 10/2014 | Dogra et al. |
| 8,876,717 B2 | 11/2014 | Tokita et al. |
| 8,879,352 B2 | 11/2014 | Witte et al. |
| 8,991,261 B2 | 3/2015 | Asao |
| 9,128,032 B2 | 9/2015 | Carson et al. |
| 9,163,980 B2 | 10/2015 | Herzog et al. |
| 9,282,899 B2 | 3/2016 | Zalev |
| 9,289,191 B2 | 3/2016 | Clingman et al. |
| 9,330,452 B2 | 5/2016 | Zalev et al. |
| 9,357,923 B2 | 6/2016 | Courtney et al. |
| 9,375,147 B2 | 6/2016 | Courtney et al. |
| 9,445,785 B2 | 9/2016 | Clingman et al. |
| 9,445,786 B2 | 9/2016 | Zalev et al. |
| 9,456,805 B2 | 10/2016 | Zalev et al. |
| 9,517,055 B2 | 12/2016 | Zalev |
| 9,528,936 B2 | 12/2016 | Schmid |
| 9,700,214 B2 | 7/2017 | Ichihara et al. |
| 2001/0022657 A1 | 9/2001 | Autrey et al. |
| 2001/0045509 A1 | 11/2001 | Al-Ali |
| 2002/0007111 A1 | 1/2002 | Deckert et al. |
| 2002/0052547 A1 | 5/2002 | Toida |
| 2002/0126961 A1 | 9/2002 | Hirabayashi et al. |
| 2003/0139672 A1 | 7/2003 | Cane et al. |
| 2003/0171677 A1 | 9/2003 | Marmarelis |
| 2003/0187319 A1 | 10/2003 | Kaneko et al. |
| 2004/0039274 A1 | 2/2004 | Benaron et al. |
| 2004/0054268 A1 * | 3/2004 | Esenaliev ........... A61B 5/14535 600/322 |
| 2004/0092811 A1 | 5/2004 | Hill |
| 2004/0147842 A1 | 7/2004 | Desmarais |
| 2004/0167619 A1 | 8/2004 | Case et al. |
| 2004/0253572 A1 | 12/2004 | Chosack et al. |
| 2005/0004458 A1 * | 1/2005 | Kanayama et al. ........... 600/437 |
| 2005/0070801 A1 | 3/2005 | Yamashita et al. |
| 2005/0075628 A1 * | 4/2005 | Cazzini ................ A61B 90/36 606/4 |
| 2005/0105877 A1 | 5/2005 | Nappi et al. |
| 2005/0187471 A1 | 8/2005 | Kanayama et al. |
| 2005/0261568 A1 | 11/2005 | Hular et al. |
| 2006/0069536 A1 | 3/2006 | Butsev et al. |
| 2006/0167531 A1 | 7/2006 | Gertner et al. |
| 2006/0171638 A1 | 8/2006 | Dye |
| 2006/0178575 A1 | 8/2006 | Piacsek et al. |
| 2006/0184042 A1 * | 8/2006 | Wang .................. A61B 5/0073 600/476 |
| 2006/0262903 A1 | 11/2006 | Diebold |
| 2006/0290926 A1 | 12/2006 | Masters et al. |
| 2007/0016049 A1 | 1/2007 | Kye |
| 2007/0081711 A1 | 4/2007 | Kim et al. |
| 2007/0093702 A1 | 4/2007 | Yu et al. |
| 2007/0106146 A1 | 5/2007 | Altmann et al. |
| 2007/0161898 A1 | 7/2007 | Hao et al. |
| 2007/0213607 A1 | 9/2007 | Mandelis et al. |
| 2007/0236492 A1 | 10/2007 | Ahn et al. |
| 2007/0238958 A1 | 10/2007 | Oraevsky et al. |
| 2008/0051655 A1 | 2/2008 | Sato et al. |
| 2008/0071172 A1 | 3/2008 | Bruck et al. |
| 2008/0114910 A1 | 5/2008 | He et al. |
| 2008/0172111 A1 | 7/2008 | Anderson et al. |
| 2008/0177183 A1 * | 7/2008 | Courtney et al. ............. 600/463 |
| 2008/0228073 A1 | 9/2008 | Silverman et al. |
| 2008/0242988 A1 | 10/2008 | Yoshida et al. |
| 2008/0255433 A1 | 10/2008 | Prough et al. |
| 2009/0000383 A1 | 1/2009 | Knowles et al. |
| 2009/0080597 A1 | 3/2009 | Basu |
| 2009/0105586 A1 | 4/2009 | Daft et al. |
| 2009/0124902 A1 | 5/2009 | Herrman |
| 2009/0136182 A1 | 5/2009 | Oshima |
| 2009/0149761 A1 | 6/2009 | Zou et al. |
| 2009/0156932 A1 | 6/2009 | Zharov |
| 2009/0171195 A1 | 7/2009 | Barbour |
| 2009/0187099 A1 | 7/2009 | Burcher |
| 2009/0220419 A1 | 9/2009 | Lopez et al. |
| 2009/0263001 A1 | 10/2009 | Ding et al. |
| 2009/0295941 A1 | 12/2009 | Nakajima et al. |
| 2009/0326898 A1 | 12/2009 | Canfield |
| 2010/0016717 A1 | 1/2010 | Dogra et al. |
| 2010/0028261 A1 | 2/2010 | Emelianov et al. |
| 2010/0049044 A1 | 2/2010 | Burcher |
| 2010/0056916 A1 | 3/2010 | Bakker et al. |
| 2010/0080427 A1 | 4/2010 | Yeluri et al. |
| 2010/0094134 A1 * | 4/2010 | Zhu et al. .................... 600/473 |
| 2010/0127171 A1 | 5/2010 | Jonsson et al. |
| 2010/0137715 A1 | 6/2010 | Kakee |
| 2010/0145416 A1 | 6/2010 | Kang et al. |
| 2010/0154547 A1 | 6/2010 | Fukada et al. |
| 2010/0174190 A1 | 7/2010 | Hancock et al. |
| 2010/0198063 A1 | 8/2010 | Huber et al. |
| 2010/0245770 A1 | 9/2010 | Zhang et al. |

(56) References Cited

U.S. PATENT DOCUMENTS

| | | |
|---|---|---|
| 2010/0249562 A1 | 9/2010 | Zhang et al. |
| 2010/0249570 A1 | 9/2010 | Carson et al. |
| 2010/0268042 A1 | 10/2010 | Wang et al. |
| 2010/0272400 A1 | 10/2010 | Bieber et al. |
| 2010/0285518 A1 | 11/2010 | Viator et al. |
| 2010/0298688 A1 | 11/2010 | Dogra et al. |
| 2011/0031059 A1* | 2/2011 | Parish .................. A61F 11/08 181/129 |
| 2011/0054292 A1 | 3/2011 | Hirson et al. |
| 2011/0088477 A1 | 4/2011 | Someda et al. |
| 2011/0091423 A1 | 4/2011 | Kempf et al. |
| 2011/0098572 A1* | 4/2011 | Chen et al. .................. 600/463 |
| 2011/0106478 A1 | 5/2011 | Someda |
| 2011/0118606 A1 | 5/2011 | Kim |
| 2011/0144495 A1 | 6/2011 | Wilkening et al. |
| 2011/0201914 A1 | 8/2011 | Wang et al. |
| 2011/0231160 A1 | 9/2011 | Suzuki |
| 2011/0238618 A1 | 9/2011 | Valdiserri et al. |
| 2011/0239766 A1 | 10/2011 | Nakajima et al. |
| 2011/0282181 A1 | 11/2011 | Wang et al. |
| 2011/0303015 A1* | 12/2011 | Ichihara ................ A61B 5/0091 73/656 |
| 2011/0306857 A1 | 12/2011 | Razansky et al. |
| 2011/0319743 A1 | 12/2011 | Satoh |
| 2011/0319744 A1 | 12/2011 | Tsujita et al. |
| 2012/0029829 A1 | 2/2012 | Li et al. |
| 2012/0054619 A1 | 3/2012 | Spooner et al. |
| 2012/0078051 A1 | 3/2012 | Suzuki et al. |
| 2012/0165677 A1 | 6/2012 | Li et al. |
| 2012/0203093 A1 | 8/2012 | Imran et al. |
| 2012/0243369 A1 | 9/2012 | Sudo et al. |
| 2013/0041267 A1 | 2/2013 | Ntziachristos et al. |
| 2013/0060140 A1 | 3/2013 | Sinelnikov |
| 2013/0064771 A1 | 3/2013 | Wada |
| 2013/0096413 A1* | 4/2013 | Ashkenazi ......... G01N 29/0654 600/407 |
| 2013/0109950 A1 | 5/2013 | Herzog et al. |
| 2013/0112001 A1* | 5/2013 | Furukawa ................ A61B 8/08 73/655 |
| 2013/0116538 A1 | 5/2013 | Herzog et al. |
| 2013/0190589 A1 | 7/2013 | Chen et al. |
| 2013/0190591 A1 | 7/2013 | Hirson et al. |
| 2013/0190595 A1 | 7/2013 | Oraevsky et al. |
| 2013/0279920 A1 | 10/2013 | Herzog |
| 2013/0281819 A1 | 10/2013 | Schmid |
| 2013/0289381 A1 | 10/2013 | Oraevsky et al. |
| 2013/0296683 A1 | 11/2013 | Herzog et al. |
| 2013/0296684 A1 | 11/2013 | Miller et al. |
| 2013/0296701 A1 | 11/2013 | Zalev et al. |
| 2013/0301380 A1 | 11/2013 | Oraevsky et al. |
| 2013/0303875 A1 | 11/2013 | Joy et al. |
| 2013/0304405 A1 | 11/2013 | Schmid et al. |
| 2013/0310688 A1 | 11/2013 | Rosen et al. |
| 2013/0335441 A1 | 12/2013 | Zalev et al. |
| 2013/0338475 A1 | 12/2013 | Herzog et al. |
| 2013/0338501 A1* | 12/2013 | Clingman ............ A61B 8/0825 600/440 |
| 2014/0005544 A1 | 1/2014 | Zalev et al. |
| 2014/0007690 A1 | 1/2014 | Hirota |
| 2014/0012138 A1 | 1/2014 | Talbert et al. |
| 2014/0039293 A1 | 2/2014 | Oraevsky et al. |
| 2014/0051969 A1 | 2/2014 | Suzuki |
| 2014/0051971 A1 | 2/2014 | Tokita |
| 2014/0052135 A1 | 2/2014 | Aman et al. |
| 2014/0058245 A1 | 2/2014 | Oishi et al. |
| 2014/0185899 A1 | 7/2014 | Zalev et al. |
| 2014/0187902 A1 | 7/2014 | Sato et al. |
| 2014/0194723 A1* | 7/2014 | Herzog et al. .................. 600/407 |
| 2014/0198606 A1 | 7/2014 | Morscher et al. |
| 2014/0221810 A1 | 8/2014 | Kacprowicz |
| 2014/0249414 A1 | 9/2014 | Herzog et al. |
| 2014/0299364 A1* | 10/2014 | Divigalpitiya .......... H05K 1/02 174/254 |
| 2014/0303476 A1 | 10/2014 | Dogra et al. |
| 2014/0323860 A1 | 10/2014 | Courtney et al. |
| 2015/0018662 A1 | 1/2015 | Ackerman, III et al. |
| 2016/0199037 A1 | 7/2016 | Clingman et al. |
| 2016/0249812 A1 | 9/2016 | Wang et al. |
| 2016/0296121 A1 | 10/2016 | Herzog et al. |
| 2016/0302763 A1 | 10/2016 | Courtney et al. |
| 2016/0317034 A1 | 11/2016 | Zalev et al. |
| 2016/0317038 A1 | 11/2016 | Zalev et al. |
| 2017/0000354 A1 | 1/2017 | Zalev et al. |
| 2017/0014101 A1 | 1/2017 | Oraevsky et al. |
| 2017/0035388 A1 | 2/2017 | Herzog et al. |
| 2017/0112474 A1 | 4/2017 | Burcher |

FOREIGN PATENT DOCUMENTS

| | | |
|---|---|---|
| EP | 1743576 A1 | 1/2007 |
| GB | 2322941 A | 9/1998 |
| JP | H10-160711 A | 6/1998 |
| JP | H11305068 A | 11/1999 |
| JP | 2003126091 A | 5/2003 |
| JP | 2003/329880 A | 11/2003 |
| JP | 2004-275270 A | 10/2004 |
| JP | 2006-020749 A | 1/2006 |
| JP | 2010090363 A | 4/2010 |
| JP | 2010125260 A | 6/2010 |
| JP | 2011072702 A | 4/2011 |
| JP | 2011097991 A | 5/2011 |
| JP | 2012-024460 A | 2/2012 |
| JP | 2012-249694 A | 12/2012 |
| JP | 2013034852 A | 2/2013 |
| JP | 2013-202050 A | 10/2013 |
| JP | 2013-255707 A | 12/2013 |
| WO | 0110295 A1 | 2/2001 |
| WO | 01-78009 A2 | 10/2001 |
| WO | 2004010866 | 2/2004 |
| WO | 2004010866 A1 | 2/2004 |
| WO | 2006061829 | 6/2006 |
| WO | 2008067842 A1 | 6/2008 |
| WO | 2010009747 A1 | 1/2010 |
| WO | 2010045421 A2 | 4/2010 |
| WO | 2011027548 A1 | 3/2011 |
| WO | 2011048788 A1 | 4/2011 |
| WO | 2011091423 A2 | 7/2011 |
| WO | 2011093069 A1 | 8/2011 |
| WO | 2011098101 A1 | 8/2011 |
| WO | WO 2011137385 A1 * | 11/2011 |
| WO | 2013/056089 A2 | 4/2013 |
| WO | 2013067304 A1 | 5/2013 |
| WO | 2013067374 A1 | 5/2013 |
| WO | 2013067383 A1 | 5/2013 |
| WO | 2013067419 A1 | 5/2013 |
| WO | 2013112626 A1 | 8/2013 |
| WO | 2013134772 A2 | 9/2013 |
| WO | 2013158154 A1 | 10/2013 |
| WO | 2013/188711 A1 | 12/2013 |
| WO | 2013/188714 A1 | 12/2013 |
| WO | 2013188707 A1 | 12/2013 |
| WO | 2013188708 A1 | 12/2013 |
| WO | 2013188709 A1 | 12/2013 |
| WO | 2013188710 A1 | 12/2013 |
| WO | 2013188713 A1 | 12/2013 |
| WO | 2014116705 A1 | 7/2014 |

OTHER PUBLICATIONS

Fronheiser et al. "Real-time optoacoustic monitoring and three-dimensional mapping of human vasculature." J. Biomed. Optics 15(2): pp. 021305(1)-021305(7). Mar./Apr. 2010.*

ISA/KR, International Search Report, Int'l Application No. PCT/US14/12553, dated May 19, 2014, p. 4.

Ermilov, Sergey A., et al. "Laser optoacoustic imaging system for detection of breast cancer." Journal of biomedical optics 14.2 (2009): 024007-024007.

Hamilton, James D., et al. "High frequency optoacoustic arrays using etalon detection." IEEE transactions on ultrasonics, ferroelectrics, and frequency control 47.1 (2000): 160-169.

Kossoff, George, Elizabeth Kelly Fry, and Jack Jellins. "Average

(56) References Cited

OTHER PUBLICATIONS velocity of ultrasound in the human female breast." The Journal of the Acoustical Society of America 53.6 (1973): 1730-1736.
Lu, Tao, and Huiyong Mao. "Deconvolution algorithm with LTI Wiener filter in photoacousic tomography." 2009 Symposium on Photonics and Optoelectronics. IEEE, 2009.
Translation of Japanese Office Action dated Feb. 2, 2018 in corresponding Japanese Application 2015555239, filed Jul. 22, 2015.
Translation of Japanese Office Action dated Oct. 24, 2017 in corresponding Japanese Application 2015555239, filed Jul. 22, 2015.
Australian Examination Report dated Jan. 12, 2018 in corresponding Australian Application 2014209521, filed Jul. 22, 2015.
Extended European Search Report dated Sep. 22, 2016 in corresponding European Application 147430128, filed Jul. 30, 2015.
Ali, Murtaza, Dave Magee, and Udayan Dasgupta. "Signal processing overview of ultrasound systems for medical imaging." SPRAB12, Texas Instruments, Texas (2008).
"MATLAB: Programming Fundamentals", The Math Works, Inc., R2011 b, 2011.
Aziz et al. 2011 Optik 122:1462-1465.
Castelino, Robin; "Biomedical Applications of Photoacoustics for Thermal Therapy", 2008.
Dahl, Jeremy J. and Trahey, Gregg E., "Off-Axis Scatterer Filters for Improved Aberration Measurements", 2003 IEEE Ultrasonics Symposium—344, 2003.
Emelianov, Stanislav Y., et al. "Combined ultrasound, optoacoustic, and elasticity imaging." Biomedical Optics 2004. International Society for Optics and Photonics, 2004.
Ermilov et al., "Development of Laser Optoacoustic and Ultrasonic Imaging System for breast cancer utilizing handheld array probes", Photons Plus Ultrasound Imaging and Sensing 2009, SPIE vol. 7177.
Esenaliev, Rinat O., et al. "Laser optoacoustic tomography for medical diagnostics: experiments with biological tissues." Photonics West'96. International Society for Optics and Photonics, 1996.
Fronheiser et al. 2010 J. Biomed. Optics 15:021305-1-021305-7.
Holan, Scott H., and John A. Viator. "Automated wavelet denoising of photoacoustic signals for circulating melanoma cell detection and burn image reconstruction." Physics in medicine and biology 53.12 (2008): N227.
Intel, Intel Integrated Performance Primitives for Intel Architecture, Reference Manual, Vol. 2: Image and Video Processing, Sep. 2007.
Karabutov, Alexander A., Vladilen S. Letokhov, and Natalia B. Podymova. "Time-resolved optoacoustic tomography of inhomogeneous media." Photonics West'95. International Society for Optics and Photonics, 1995.
Kingsbury, "Complex Wavelets for Shift Invariant Analysis and Filtering of Signals", Journal of Applied and Computational Harmonic Analysis, vol. 10, No. 3, May 2001, pp. 234-253.
Kuchment, P. et al., "Mathematics of Photoacoustic and Thermoacoustic Tomography", Mathematics Dept., Texas A&M University, Dec. 10, 2009.
Ma, Rui, et al. "Multispectral optoacoustic tomography (MSOT) scanner for whole-body small animal imaging." Optics express 17.24 (2009): 21414-21426.

Misiti, Michel et al., "Wavelet Toolbox", The MathWorks, Inc., User's Guide, Version 1, 1996.
Munch, Beat et al., "Stripe and ring artifact removal with combined wavelet—Fourier filtering", Optics Express 8567, vol. 17, No. 10, May 11, 2009.
Needles A et al: "Development and validation of a combined photoacoustic micro-ultrasound system foroxygen saturation estimation", Photons Plus Ultrasound: Imaging and Sensing 2011, SPIE, 1000 20th St. Bellingham WA 98225-6705 USA, vol. 7899, No. 1, Feb. 10, 2011 (Feb. 10, 2011), pp. 1-8.
Nguyen, "A Family of Inversion Formulas in Thermoacoustic Tomography", Department of Mathematics, Texas A&M University, Mar. 5, 2009.
Niederhauser et al. "Combined Ultrasound and Optoacoustic System for Real-Time High-Contrast Vascular Imaging in Vivo," IEEE Trans. Med. Imaging, vol. 24, No. 4, pp. 436-440, 2005.
Niederhauser, Joel J., Michael Jaeger, and Martin Frenz. "Comparision of laser-induced and classical ultasound." Biomedical Optics 2003. International Society for Optics and Photonics, 2003.
O'Donnell, Matthew et al., "Correlation-Based Aberration Correction in the Presence of Inoperable Elements", IEEE Transactions of Ultrasonics, Ferroelectrics, and Frequency Control, vol. 39, No. 6, Nov. 1992.
Oraevsky, A. A., et al. "Time-resolved optoacoustic imaging in layered biological tissues." Advances in optical imaging and photon migration 21 (1994): 161-165.
Oraevsky, Alexander A., et al. "Direct measurement of laser fluence distribution and optoacoustic imaging in heterogeneous tissues." International Symposium on Biomedical Optics Europe'94. International Society for Optics and Photonics, 1995.
Oraevsky, Alexander A., et al. "Laser optoacoustic tomography for medical diagnostics: Principles." Photonics West'96. International Society for Optics and Photonics, 1996.
Oraevsky, Alexander A., et al. "Lateral and z-axial resolution in laser optoacoustic imaging with ultrasonic transducers." Photonics West'95. International Society for Optics and Photonics, 1995.
Oraevsky, Alexander A., Steven L. Jacques, and Frank K. Tittel. "Determination of tissue optical properties by piezoelectric detection of laser-induced stress waves." OE/LASE'93: Optics, Electro-Optics, & Laser Applications in Science& Engineering. International Society for Optics and Photonics, 1993.
Otto et al., "Coregistration of Angiogenesis Related Hemoglobin and Tissue Density in breast tumors using opto-acoustic imaging combined with ultrasound", 2009.
Robert J Talbert et al, "Photoacoustic discrimination of viable and thermally coagulated blood using a two-wavelength method for burn injury monitoring; Photoacoustic blood discrimination", Physics in Medicine and Biology, Institute of Physics Publishing, Bristol GB, (Apr. 7, 2007), vol. 52, No. 7.
Sendur et al., "Bivariate Shrinkage Functions for Wavelet-Based Denoising Exploiting Interscale Dependency", IEEE Transactions on Signal Processing, vol. 50, No. 11, Nov. 2002.
Xueding Wang et al: "Noninvasive imaging of hemoglobin concentration and oxygenation in the rat brain using high-resolution photoacoustic tomography", Journal of Biomedical Optics, vol. 11, No. 2, May 3, 2006 (May 3, 2006), p. 024015, XP055202984, ISSN: 1083-3668, DOI: 10.1117/1.2192804.

\* cited by examiner

PROBE WITH OPTOACOUSTIC ISOLATOR

CROSS-REFERENCE

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present invention relates in general to the field of medical imaging, and in particular to a probe with an optoacoustic isolator for use in medical imaging.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION

Figure 1:
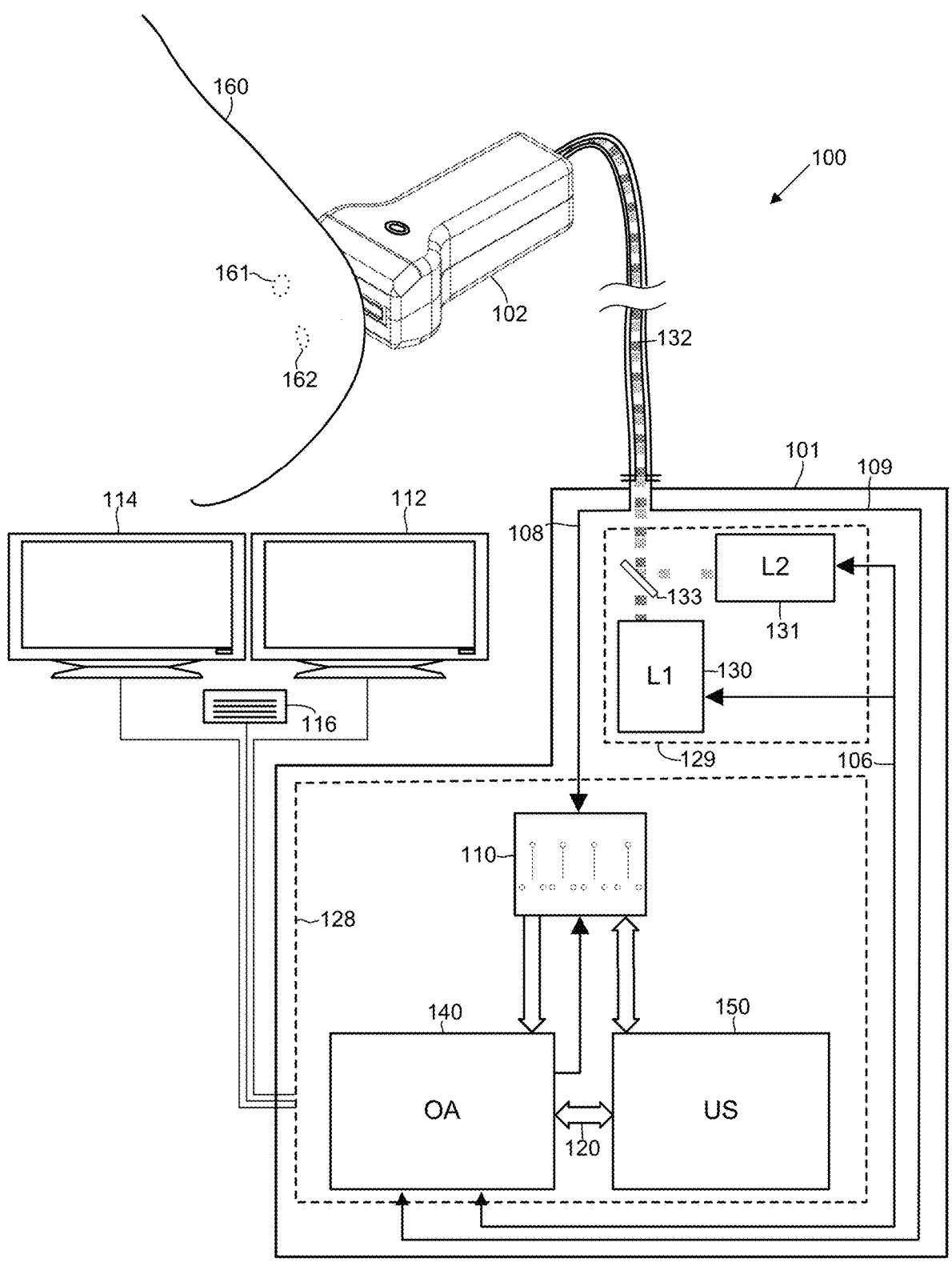
FIG. 1 shows a schematic block diagram illustrating an embodiment of a combined optoacoustic and ultrasound system that may be used as a platform for the methods and devices disclosed herein.

Reference will now be made in detail to various embodiments of the present invention, examples of which are illustrated in the accompanying drawings.

Generally, device 100 provides an optoacoustic system that may also be employed as a multi-modality, combined optoacoustic and ultrasound system. In an embodiment, the device 100 includes a probe 102 connected via a light path 132 and an electrical path 108 to a system chassis 101. Within the system chassis 101 is housed a light subsystem 129 and a computing subsystem 128. The computing subsystem 128 includes one or more computing components for ultrasound control and analysis and optoacoustic control and analysis; these components may be separate, or integrated. In an embodiment, the computing subsystem comprises a relay system 110, an optoacoustic processing and overlay system 140 and an ultrasound instrument 150.

The light system 129 is capable of producing pulses of light of at least two different wavelengths. In an embodiment, the light system 129 output should be capable of producing short pulses of light in each of those wavelengths, e.g., a pulse lasting less than about 100 ns, and more preferably around 5 ns. As will be apparent to one of ordinary skill in the art from this disclosure, the inventions disclosed herein may also be practiced using pulsed light comprising pulses lasting greater than 100 ns. In an embodiment, the light source 129 includes two separate lights 130, 131. The output of the light system 129 is delivered to the probe 102 via the optical path 132. In an embodiment, the lights 130, 131 are lasers producing light in the infrared, near-infrared, and/or visible spectrum. In an embodiment, light 130 and light 131 each produce light at a different wavelength in the infrared or near-infrared spectrum. In an embodiment, the optical path 132 used to deliver light from the light source 129 to the probe 102 is a fiber optic bundle comprising multiple strands of optical fiber. In an embodiment, the optical path 132 comprises sufficient optical fibers of sufficient size (diameter) to carry a short, high powered pulse of light to the distal end of the optical path 132. In an embodiment, the total pulse energy carried over the optical path 132 may be on the order of one or more millijoules. In an embodiment, the total energy per light pulse carried over the optical path 132 is less than about 100 millijoules. In an embodiment, the total energy per light pulse carried over the optical path 132 is in the range of about 10-30 millijoules, and the optical path 132 comprises around 1,000 optical fibers of about 150 microns each. In an embodiment, a single fiber can be used as the optical path. In such embodiment, the fiber may be 400-1500 microns in diameter. Of course, the diameter of such single fiber may be smaller, e.g., 400 microns. Given the required total pulse energy carried over the fiber, one skilled in the art can calculate the diameter required of the fiber accordingly.

In an illustrative embodiment, the light system 129 may use Nd-YAG and Alexandrite lasers as its two lights 130, 131, although other types, and additional lights, may also be used. Lights 130, 131 should be capable of producing a short pulse of light, e.g., a pulse lasting less than about 100 ns, and more preferably around 5 ns. In an embodiment, the two lights 130, 131 can be separately triggered. In an embodiment, the light output by the lights 130, 131 may be projected onto the same light path 132 through the use of an optical element 133 that generally permits one light 130 to pass through from a first side to a second side, while reflecting one light 131 that strikes the second side. The use of optical element 133 or a similar element permits the alignment of the output of two lights 130, 131 such as lasers onto proximal end of the light path 132. In an embodiment, optical elements 133 can align the light output from more than two lasers, for example, through the use of multiple optical elements 133. In an embodiment, multiple light systems and light paths may be employed, with the light of each light system being carried on separate fibers that are intermingled at their distal ends.

Although the total energy per light pulse carried over the optical path is in the order of tens of millijoules, because the pulse of lights 130, 131 is so short, the peak power output over the optical path 132 is frequently approaching or in the megawatt range. Accordingly, the output of lights 130, 131 has the capacity to cause the optical fibers and/or the cladding on the optical fibers to burn. Burnt optical fibers and burnt cladding can exacerbate the problem as they begin to transmit less light power and cause more heating. Accordingly, in an embodiment, sufficient number and size optical fibers are present in the optical path 132 to permit handling of the peak power loads and avoid fiber burnout. To accommodate higher peak power, a larger fiber bundle can be used. It will be apparent to a person of skill in the art that the peak power capacity of a fiber bundle can be increased by increasing the number of optical fibers, or the diameter of optical fibers, or both. Notably, however, as the dimension of the fiber bundle increases, the weight and flexibility of the optical path 132 decreases. Moreover, when using more optical fibers, or optical fibers of a larger diameter, the output of light source 129 must be delivered to the optical path 132 across the wider diameter of the larger bundle. In an embodiment, regardless of the ultimate size of the proximal end of light path 132, the output of light source 129 should be distributed sufficiently across its cross section to prevent burn-out failures when operating in expected peak power ranges.

In an embodiment, the fibers of the proximal end of the light path 132 may be fused to form a fused entry point to the optical path 132 for the output of light source 129. In an embodiment, the fiber ends can be fused by applying heat. Once the proximal end of optical path 132 has been fused, it will resist burnout at substantially higher peak power. For example, using a fused end light path 132 may permit carriage of three, four or even five times as much peak power. The ability to carry substantially higher peak power in a given optical path 132 permits use of a more flexible and lighter fiber optic bundle to carry the same peak power as an un-fused optical path 132. Thus, in an embodiment, where a ½ fiber optic bundle may have been required in an un-fused bundle of optical fibers forming an optical path, a ¼" fiber optic bundle with a fused proximal end may be used to carry the same peak power. A ¼" fiber optic bundle with a fused proximal end is approximately ¼ of the weight and much more flexible than a ½ fiber optic bundle. Moreover, fusing of the proximal end of light path 132 may produce an even smaller fused area to illuminate using light source 132 as the fusing removes the inter-fiber spaces that would have existed in the bundled end of the round-cross-section optical fibers. Accordingly, one or more of the following advantages may be attained by fusing the proximal end of the optical fibers comprising the light path 132: reduced weight of the light path; increased flexibility of the light path; reduced failure; increased reliability; higher peak power capacity.

In an embodiment, the light output by the lights 130, 131 is sent towards a fused optical fiber bundle at the proximal end of light path 132 via an optical path, which may include optical element 133, internal to the light source 129. In an embodiment, light source 129 is a laser system capable of outputting laser light pulses, at one or more wavelengths, onto light path 132. In an embodiment, light path 132 is a fiber optic bundle having a fused end proximal to the light source 129.

In an embodiment, the device 100 also comprises an electrical path 108 running to and/or from the probe 102 to a relay system 110 within the system chassis 101. The electrical path 108 may run near, alongside or coaxially with the optical path 132 from the probe 102 toward their respective connections on the system chassis 101. In an embodiment, the electrical path 108 comprises a plurality of separate coaxial wires. In an embodiment, the electrical path 108 is run in a common jacket with at least a portion of the optical path 132. Running electrical path 108 in a common jacket with at least a portion of the optical path 132 reduces the number of cables running from the system chassis 101 to the probe 102. Running electrical path 108 in a common jacket with at least a portion of the optical path 132 may minimize the diameter and weight of, and increase the durability of, the combined cables (i.e., optical path 132 and electrical path 108) running from the system chassis 101 to the probe 102.

In an embodiment, the plurality of coaxial wires is woven around at least a portion of the optical path 132. As discussed above, many considerations go into the number of separate optical fibers used in optical path 132. As discussed further below, numerous design considerations go into the number of separate electrical leads or traces forming the electrical path 108. In an embodiment, there are about 256 leads (corresponding to 256 transducers) forming the electrical path 108 and approximately 1,000 separate optical fibers forming the optical path 132, making the fiber:lead ratio about 4:1. As will be apparent, it is possible to comingle the optical fibers and leads or traces in the electrical path in a variety of ways, including, for example, bundling a group of individual fibers with a single electrical lead or trace, or bundling proportionally larger groupings of fibers and leads together. In an embodiment, the bundling of fibers and leads or traces would be done generally in the proportion of fibers:leads in the system.

One or more displays 112, 114, which may be touch screen displays, are provided for displaying images and all or portions of the device 100 user interface. One or more other user input devices (not shown) such as a keyboard, mouse and various other input devices (e.g., dials and switches) may be provided for receiving input from an operator. As an option, power and control signal lines 109 carry power to the probe 102 and control signals between the probe 102 and the computing subsystem 128.

Figure 2:
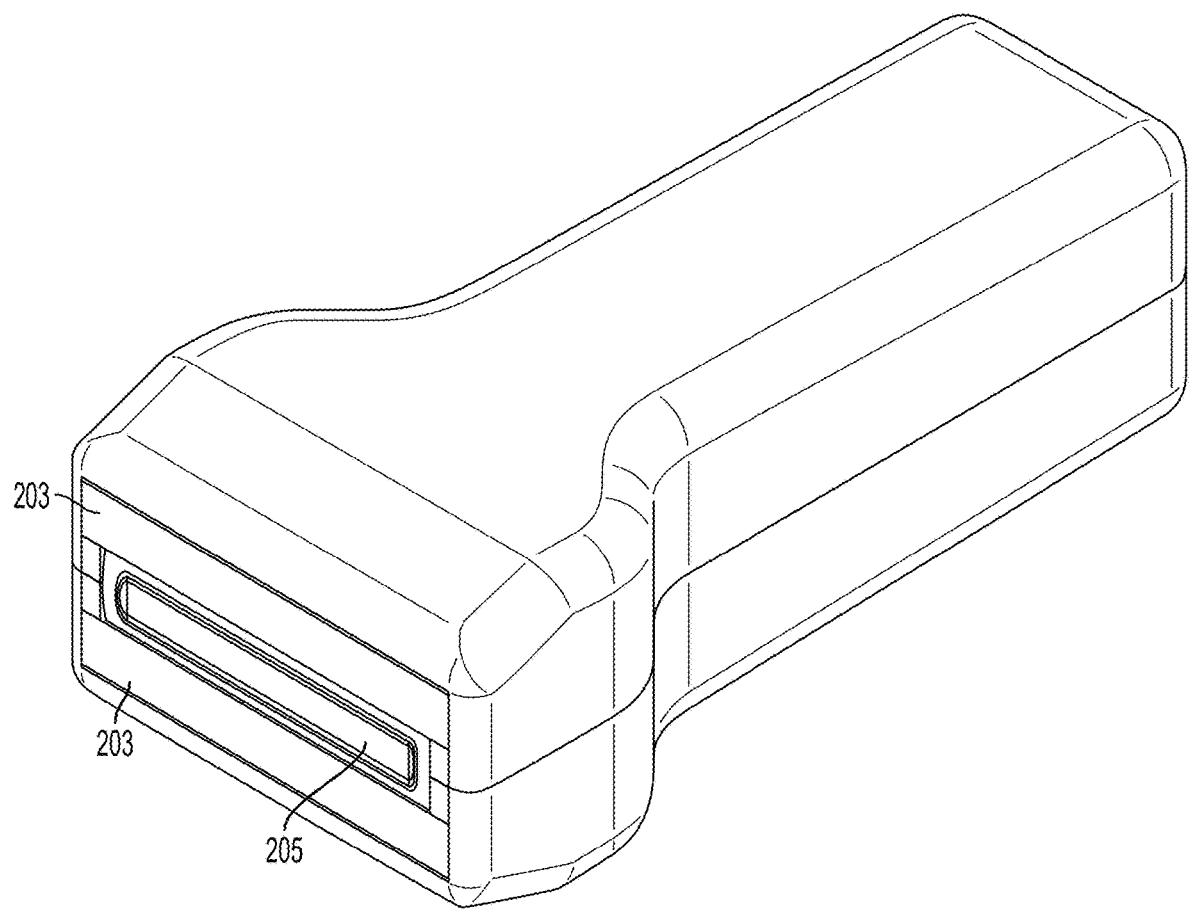
FIG. 2 shows a schematic orthogonal view of an embodiment of a probe that may be used in connection with the methods and other devices disclosed herein.

Turning now to FIG. 2, the probe 102 includes an array of ultrasound transducer elements forming an ultrasound transducer (not shown) covered by an acoustic lens 205. In an embodiment the ultrasound transducer comprises an array of piezoelectric elements that can both transmit and receive acoustic energy. In an embodiment, at least some of the ultrasound transducer elements are capable of detecting ultrasound frequencies over a wide range. For example, ultrasound transducer elements may be capable of detecting ultrasound in the range from about 50 Khz to 20 Mhz. This range can be achieved by applying a high impedance load (e.g., in the range of 5,000 to 50,000 ohms) to achieve a lower frequency response. The ultrasound transducer elements are capable of generating electrical energy in response to receiving ultrasound acoustic energy. The electrical energy generated by the ultrasound transducer elements receiving ultrasound is transmitted to the computing subsystem 128 via electrical path 108.

The probe 102 also includes one or more optical windows 203 through which the light carried on optical path 132 can be transmitted to the surface of a three-dimensional volume 160. In an embodiment, it is desirable to locate one side of the optical window 203 as close as practical to the acoustic lens 205. The total area of an optical window 203 is important to maximize energy for a given fluence incident on the surface of the volume 160.

In an embodiment, the multiple strands of optical fiber making up the optical path 132 are terminated in two light bars (not shown). In an embodiment, the ultrasound transducer elements (not shown) are arranged in an array that runs along a geometric plane and are generally spaced equidistant from each other. In an embodiment, the light bars (not shown) are oriented longitudinally, on each side of the planar array of ultrasound transducer elements. Preferably the ultrasound transducer elements generate electrical energy in response to both ultrasound acoustic energy received in response to stimulation caused by the pulsed light sources 130, 131 and to ultrasound acoustic energy received in response to acoustic output of the ultrasound transducer elements.

Referring back to FIG. 1, in use, the probe 102 may be placed in close proximity with organic tissue, phantom or other three-dimensional volume 160 that may have one or more localized inhomogeneities 161, 162, such as e.g., a tumor, within. An ultrasound gel (not shown) or other material may be used to improve acoustic coupling between the probe 102 and the surface of the volume 160. The probe 102, when in proximity with the surface of the volume 160, can emit a pulse of a light through the optical windows 203 or an ultrasound through acoustic lens 205, and then generate electrical energy corresponding to ultrasound detected in response to the emitted light or sound.

In an embodiment, the computing subsystem 128 can trigger activity from light system 129 over control signal line 106. In an alternative embodiment, the light system 129 can create the trigger signal and inform the computing subsystem 128 of its activity over control signal line 106. Such information can be used to by the computing subsystem 128 to begin the data acquisition process. In this respect, it is noted that communication over control signal line 106 can flow both ways between the computing subsystem 128 (and/or the optoacoustic processing and overlay system 140 therein) and the light system 129.

In an embodiment, computing subsystem 128 can utilize control signal line 106 to control the start time and duration of light pulses from each light source 130, 131. The computing subsystem 128 can also trigger the probe 102 to emit ultrasound acoustic energy via the ultrasound transducer elements behind the acoustic lens 205.

In an embodiment, the computing subsystem 128 receives electrical signals representative of the ultrasound detected by the ultrasound transducer elements, in response to an ultrasound transmitted signal or an optically generated ultrasound signal, behind the acoustic lens 205 via electrical path 108. In an embodiment, the electrical signal representative of the ultrasound detected by the ultrasound transducer elements behind the acoustic lens 205 is the analog electrical signal created by the elements themselves. In such embodiment, the electrical signals representative of the ultrasound detected by the ultrasound transducer elements behind the acoustic lens 205 is transmitted to the computing subsystem via electrical path 108, and electrical path 108 is selectively directed by relay system 110 to the optoacoustic processing and overlay system 140 or the ultrasound instrument 150 for processing of the detected ultrasound. In such embodiment, the ultrasound instrument 150 can receive the same input (over the same connector) as it would receive from an ultrasound probe.

In another embodiment, the electrical signal representative of the ultrasound detected by the ultrasound transducer elements behind the acoustic lens 205 is digitized by an analog-to-digital converter which can be housed in the probe 102. In such embodiment, time-resolved electrical signal representative of the ultrasound detected by the ultrasound transducer elements behind the acoustic lens 205 is transmitted across the electrical path 108. Where the electrical signal is digitized at the probe 102, as will be apparent to one of skill in the art, the relay system 110 may be implemented to deliver digital data to the optoacoustic processing and overlay system 140 or the ultrasound instrument 150, or may not be needed at all.

The signal representative of the ultrasound detected by each of the plurality of ultrasound transducer elements behind the acoustic lens 205 may be carried on a separate wire over the electrical path 108. Alternatively, the signal representative of the ultrasound detected by a plurality of ultrasound transducer elements behind the acoustic lens 205, or even all of the ultrasound transducer elements behind the acoustic lens 205, may be multiplexed (e.g., time division or frequency division) utilizing a multiplexer in the probe and a demultiplexer in the computing subsystem 128.

In an embodiment, the ultrasound instrument 150 processes ultrasound-induced acoustic signals to produce ultrasound images and the optoacoustic processing and overlay system 140 processes light-induced acoustic signals to produce optoacoustic images. In an embodiment, the ultrasound instrument 150 and optoacoustic processing and overlay system 140 can be combined into an integrated system performing the combined functions of both. As discussed above, in an embodiment, electrical signals representative of ultrasound detected by the probe 102 and delivered to the computing subsystem 128 via electrical path 108 is switched between the ultrasound instrument 150 and the optoacoustic instrument 140 via relay system 110 in accordance with whether the signal results from ultrasound stimulation or light stimulation.

In an embodiment, tomographic images reflecting the ultrasound-stimulated data may be generated by the ultrasound instrument 150 and tomographic images reflecting the light-stimulated data may be generated by the optoacoustic processing and overlay system 140.

Images, including tomographic images, produced by the optoacoustic processing and overlay system 140 can be stored in a computer memory in that system, along with data associated with sequence or time and date of the image data that was captured. Images, including tomographic images, produced by the ultrasound instrument 150 may be transmitted to the optoacoustic processing and overlay system 140 via a suitable interface 170, where they can be stored, along with images generated from the light-stimulated data, in a time-synchronized manner. In an embodiment, images stored in the memory of the optoacoustic processing and overlay system 140 can be recorded to another memory, e.g., a non-volatile memory internal to, or external to, the device.

In an embodiment, the optoacoustic processing and overlay system 140 can overlay images produced by the ultrasound instrument with images produced by optoacoustic instrument 140 for storage in the memory and/or display on one or more monitors 112, 114. In an embodiment, the overlayed optoacoustic image may be shown in a distinct color to distinguish it from the ultrasound image. In an embodiment, the overlaid optoacoustic image may contain colors that correspond to details discernable through optoacoustic imaging, such as, for example, blood oxygenation. In an embodiment, oxygenated blood is shown more in red than blue, while deoxygenated blood is shown in more blue than red. As used herein, the expression overlaid includes merging of the image by mixing as well as traditional overlaying of the image.

In an embodiment, the device 100 may be configured to operate in a cycle comprising a sequence of successively generating and acquiring data relating to one of the device's modalities, i.e., ultrasound or optoacoustic. The minimum time spacing between operation of the device's modalities depends on the device 100 components and their ability to fully execute and recycle for use. In an embodiment, a user can select between a variety of preprogrammed cycles such as: ultrasound only; wavelength one only; wavelength two only; wavelength one and two; and multiple iterations of wavelength one and two followed by ultrasound. Other combinations will be apparent to one of skill in the art. In an embodiment, additional cycles can be added by the machine operator. In an embodiment, the data collection of an entire cycle is generally intended to be directed to substantially the same portion of volume 160 and to be accomplished in rapid succession. In an embodiment, the device 100 cycles are normally in the range of 1 to 50 per second, and more typically in the range of 2 to 20 per second, as discussed above. The maximum cycle frequency is limited only by the capabilities of the cycle and modalities.

In an embodiment, the displays 112, 114 of device 100 can be configured to show various information depending upon the selected operating cycles. In an embodiment, any display 112, 144 or portion of the display can show at least one of the following: an ultrasound only image; a first wavelength response only image; a second wavelength response only image; a combined first and second wavelength response image; and/or an overlay ultrasound image and a wavelength response or combined wavelength response image. The combined first and second wavelength image may comprise a differential or other combinatorial means to provide the image. In an embodiment, an image can be displayed corresponding to each of the separate data collections in a cycle, or corresponding to the sum or difference between any or all of them.

In an embodiment, the device can be operated using a three-phase data collection operation, one phase generating and collecting data in response to ultrasound stimulus, one phase generating and collecting data in response to a first wavelength of light, and one phase generating and collecting data in response to a second wavelength of light.

Using proper wavelength(s), optoacoustics is effective in identifying blood within a volume 160, and using multiple wavelengths can be used to readily distinguish between oxygenated and deoxygenated blood. Similarly, using proper wavelengths, optoacoustics is effective for measuring localized hemoglobin content within a volume 160. Thus, for example, a malignant tumor, which is characterized by increased blood concentration and decreased oxygenation, will appear very differently in an optoacoustic image than a benign growth, which is not characterized by such an increased blood concentration and has more normal oxygenation. Moreover, specific wavelengths of light can be selected to better distinguish between various biological tissues and organs. While a large spectrum of infrared, near-infrared and visible wavelengths can produce optoacoustic response in biological entities, oxygenated blood is more optoacoustically responsive than deoxygenated blood to a light source having a wavelength of about 1064 nm, while deoxygenated blood is more optoacoustically responsive than oxygenated blood to a light source having a wavelength of 757 nm. The number and specific wavelength(s) of light used in the device 100 are selected in accordance with the makeup of the volume and the type of target that is of interest.

Figure 3:
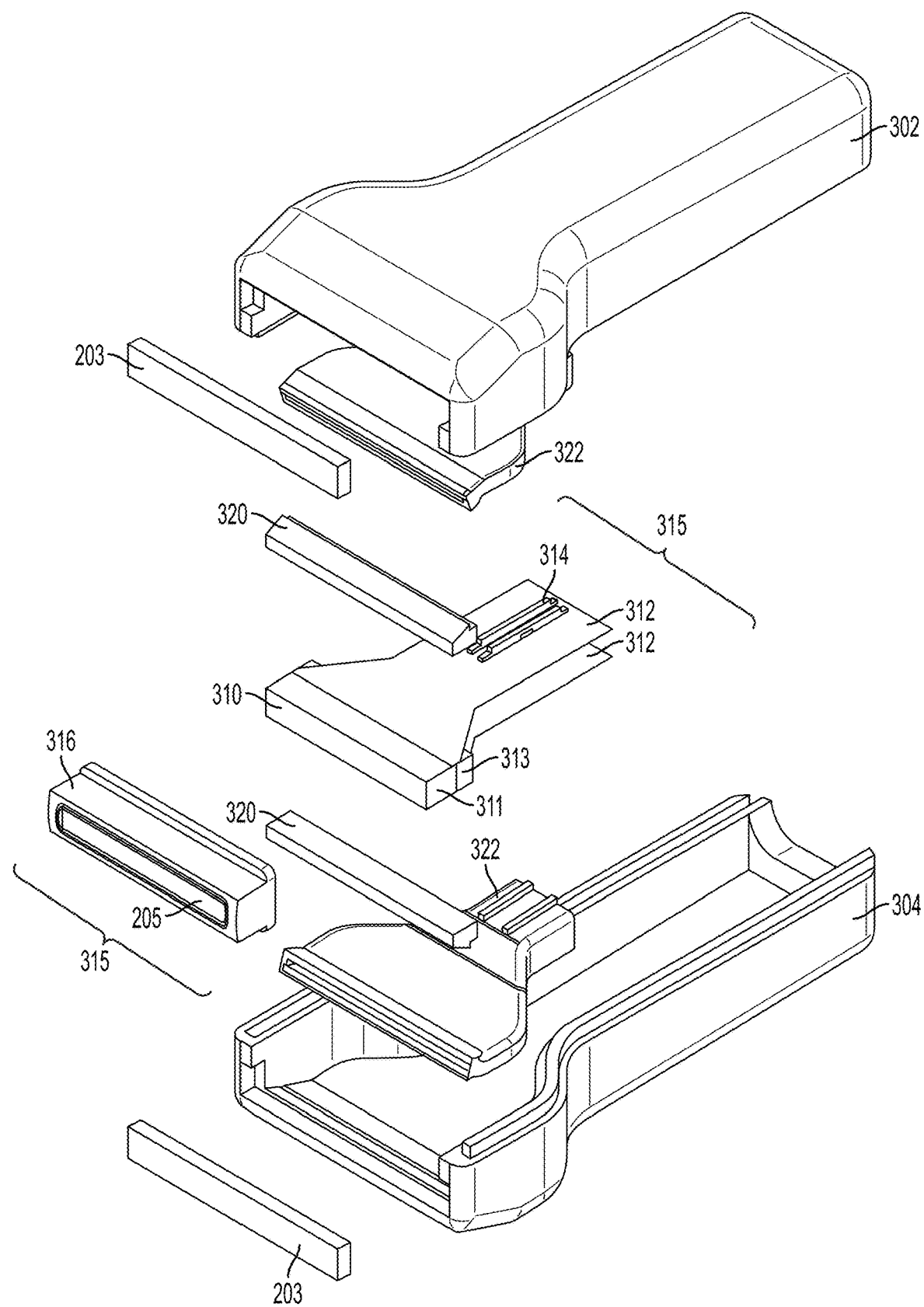
FIG. 3 shows an exploded view of an embodiment of the probe shown in FIG. 2.

FIG. 3 shows an exploded view of an embodiment of the probe 102 shown in FIG. 2. Shells 302, 304 are separated to show the components within the probe 102. The shells 302, 304 may be made from plastic or any other suitable material. The surfaces of the shells 302, 304 that may be exposed to light, and especially light generated by the light subsystem 129, are preferably both reflective (i.e., light colored) material and light scattering (i.e., having a scattering coefficient between 1 and 10). In an embodiment, the surfaces of the shells 302, 304 are highly reflective, i.e., more than 75% reflective. In an embodiment, the surfaces of the shells 302, 304 are very highly reflective, i.e., more than about 90% reflective. In an embodiment, the surfaces of the shells 302, 304 have low optical absorption, i.e., less than 25% absorptive. In an embodiment, the surfaces of the shells 302, 304 have very low optical absorption, i.e., less than about 10% absorptive. In addition, the material forming the shells 302, 304 should be acoustically absorbent to absorb, rather than reflect or transmit acoustic energy. In an embodiment, white plastic shells 302, 304 are used.

In an embodiment, flex circuit 312 comprises a plurality of electrical traces (not shown) connecting cable connectors 314 to an array of piezoelectric ultrasound transducer elements (not shown) forming ultrasound transducer 310. In an embodiment, flex circuit 312 is folded and wrapped around a backing 311, and may be secured thereto using a bonding agent such as silicon. In an embodiment, a block 313 is affixed to the backing 311 opposite the array of piezoelectric ultrasound transducer elements. In an embodiment, the ultrasound transducer 310 comprises at least 128 transducer elements, although it may be desirable to have a greater numbers of transducer elements, as additional elements may reduce distortion, and/or increase resolution, accuracy and/or depth of imaging of the device 100. The cable connectors 314 operatively connect the electrical traces, and thus, the ultrasound transducer 310, to the electrical path 108. In an embodiment, the electrical path 108 includes a coaxial wire for each ultrasound transducer element in the ultrasound transducer array 310.

The ultrasound transducer 310 fits within housing 316 so that the transducer elements are in close proximity to, or in contact with an acoustic lens 205. The acoustic lens 205 may comprise a silicon rubber, such as a room temperature vulcanization (RTV) silicon rubber. In an embodiment, the housing 316 and the acoustic lens 205 are formed as a single unit, from the same RTV silicon rubber material. In an embodiment, the ultrasound transducer 310, portions of the flex circuit 312, backing 311 and block 313 are secured within the housing 316 including an acoustic lens 205 using a suitable adhesive such as silicon to form a transducer assembly 315. The block 313 can be used to affix or secure the transducer assembly 315 to other components.

To whiten, and reduce the optoacoustic effect of light generated by the light subsystem 129 on an RTV silicon rubber acoustic lens 205 and/or the transducer assembly 315, in an embodiment, the RTV silicon rubber forming the acoustic lens 205 and/or the transducer assembly 315 may be doped with $TiO_2$. In an embodiment, the RTV silicon rubber forming the acoustic lens 205 and/or the transducer assembly 315 may be doped with approximately 4% $TiO_2$. In an embodiment, the outer surface of the acoustic lens 205 and/or the outer surface of the transducer assembly 315 may additionally be, or alternatively be, coated with a thin layer of metal such as brass, aluminum, copper or gold. Gold, however, has been found to have a tendency to flake or crack off of RTV silicon rubber. It has been found that the RTV silicon may be first coated with parylene, then coated with nickel, then coated with gold, and finally, again, coated with parylene. The multiple layering provides a durable gold coating without any substantial adverse effect to the acoustic properties of the acoustic lens 205, and without any substantial adverse effect to the transducer assembly 315 to detect ultrasound. In practice, it has been found that the parylene coatings beneath the nickel and over the gold layers, may curl at the edges rather than adhering well to the metals or rubber upon which it is deposited. Thus, as discussed in more detail below, in an embodiment, the portions of the acoustic lens 205 and/or transducer assembly 315 having a parylene coating edge are adapted to be mechanically secured against other components to prevent curling or peeling. In an embodiment, substantially the entire outer surface of the transducer assembly 315, including the acoustic lens 205, are coated with continuous layers of parylene, then nickel, then gold and then parylene again.

In an embodiment, a reflective material surrounds the transducer assembly 315 from the rear edge of the housing 316 to the end of the flex circuit 312 to reflect any light from the light path 132 that may be incident upon its surfaces. In an embodiment, an electromagnetic shield for RF energy surrounds the transducer assembly 315 from the rear edge of the housing 316 to the end of the flex circuit 312. In an embodiment, the lights 130, 131, may draw substantial energy (e.g., more than 1,000 volts for a few nanoseconds) creating substantial electromagnetic RF energy in the area of the probe 102. In an embodiment, the transducer assembly 315 from the rear edge of the housing 316 to the end of the flex circuit 312 is surrounded by a foil, which may act as a reflective material and an RF energy shield. In an embodiment, the foil is selected from the group: copper, gold, silver. In an embodiment, the foil is tied into the device's 100 electrical ground.

Spacers 320 space and position the light bar guide 322 with respect to the transducer assembly 315. Spacers are preferably made from materials that reduce its optoacoustic response to light generated by the light subsystem 129. In an embodiment, the spacers 320 are made from a material similar to the light contacting portions of the shells 302, 304. In an embodiment, the light bar guide 322 encases optical fibers that are part of the light path 132. In an embodiment, the optical fibers making up the light path 132 may be randomly (or pseudo-randomly) distributed throughout the light bar guide 322, thus making specific locations on the light receiving end of the fiber optic bundle at least pseudo-random with respect to corresponding specific locations on the light emitting end of the optical fibers retained by the light bar guide 322. As used herein the term randomly (or pseudo-randomly) distributed optical fibers making up the light path 132 means that the mapping of fibers from the proximal end to the distal end is done such that a localized interference in the light path 132 (e.g., burnout of a group of adjacent optical fibers) or a localized phenomenon (e.g., non-uniform light at the entry point to the optical path 132) will have an effect on the overall power transmitted, but will not have an operationally significant effect on any specific part of the distal end of the light path 132. Thus, two optical fibers adjacent at the proximal end are unlikely to be adjacent at the distal end of the optical path 132. Where optical fiber bundles are fused at the proximal and distal ends, the randomization must be done before at least one end is fused. As used herein the term randomly (or pseudo-randomly) distributed optical fibers does not mean that two different optical paths 132—i.e., for different devices 100—must differ from each other. In other words, a single "random" mapping may be reproduced in the light path of different devices 100 while still meeting the criteria of being a randomized. Because light generally behaves in a Gaussian manner, the entry point to the light path 132 is typically less than perfectly uniform. Randomization, as discussed above, may accommodate for the non-uniform entry of light into the light path 132. Randomization may also provide homogenization of light fluence over area illuminated, as it may aid in more evenly distributing the light fluence.

In an embodiment, the optical fibers encased by a light bar guide 322 all end on substantially the same geometric surface, e.g., a curved or flat plane. In one embodiment, after the fibers have been attached to the light bar guide 322, the fiber ends may be lapped and polished to provide for a more uniform angle of light emission. In an embodiment, the light bar guide 322, as installed in the assembled probe 102, directs the light emitting there-from at an angle slightly less than normal to the distal face of the probe 102, and specifically, at small angle inwards, towards the plane normal to and intersecting the center of the acoustic transducer array 310. In an embodiment, the distal end(s) of the optical path 132 should match—or closely approximate the shape of the acoustic transducer array 132.

The term bar, as used in "light bar guide" herein is not intended to import a specific shape. For example, the light bar guide 322 may guide the distal ends of optical fibers into substantially any shape such as, without limitation, a whole or part of a circle, oval, triangle, square, rectangle or any irregular shape.

In an embodiment, one or more light bar guides 322 and optical windows 203 are external to the shells 302, 304 housing the acoustic transducer assembly 315, and are adapted to be attached to the outer sides of one or more of the shells 302, 304.

In an embodiment, the angle of light emitting from the optical window 203 may be adjustable. In an embodiment, the light emitting from the optical window 203 may be adjustable across a range. At one end of the range, light may emit from the optical window 203 in a direction normal to the distal face of the probe 102, and at the other end of the range light may emit from the optical window 203 at an inward angle of up to 45 degrees or more towards the plane normal to and intersecting the center of the acoustic transducer array 310. The range can be smaller or larger.

In an embodiment wherein a probe has two optical windows 203, the angle of light emitting from both optical windows 203 can be adjustable, individually, or together. Where adjusting the angle of light emitting from both optical windows 203 together, the light direction would, in each case increase or decrease the angle of inward projection, that is, projection towards the plane normal to and intersecting the center of the acoustic transducer array 310. In this manner, a larger light fluence can be directed deeper into the volume 160 (by angling toward normal), or shallower (by angling more inwardly).

Controlling the direction of the light angle can be done by moving the light guide 322, or it can be accomplished optically through the use of post-light path 132 optics. Optical solutions may include the use of one or more lenses and/or prisms to re-direct the light that has been transmitted through the light path 132. Re-directed light can be directed to illuminate a desired area, such as an area directly beneath the transducer elements 310. Controlling the direction of light transmitted by the probe 102 is useful to maintain safe and optimize the direction of the light with respect to the skin and the transducers.

Control line 109 may be used to send commands redirecting light and/or to report the actual direction of light at the time a light pulse is emitted from the light path 132. The angle of the light emitting from the optical window 203 may be important data to consider when interpreting acoustic information resulting from the light pulse.

In an embodiment, the device 100 can adjust the angle of incident laser light emitting from the probe 102. Adjustment of the angle of incident laser light emitting from the probe 102 may be carried out under the control of commands which may be sent via control line 109, or may be manually carried out. In an embodiment, a standoff may be used, e.g., to help direct incident laser light to the desired depth, or closer to the surface than can be achieved without a standoff. In an embodiment, the standoff is relatively transparent to both acoustic and light, and preferably to acoustics in the ultrasound range and light one or more of the wavelengths utilized by the light source 129. While the use of standoffs is known in ultrasound applications to aid in imaging of objects close to the surface of the volume 160 because ultrasound resolution lacks the capability to detect objects at a nominal distance from its transducers, the use of a standoff in the present application is for a different purpose, namely, to allow the light sources to be aimed directly under the transducer elements 310. In an embodiment, the standoff is separate from the probe 102, and placed between the volume 160, and the distal end of the probe 102 comprising the acoustic lens 205 and one or more optical windows 203. In an embodiment, the standoff may be integral to the probe, and may be move into place and withdrawn as desired.

Optical windows 203 may also be part of the probe 102 assembly. In an embodiment, the optical windows 203 is spaced from the end of the light bar guide 322, and thus, from the ends of the optical fibers making up the light path 132. The term optical window, as used here, is not limited to mechanically or optically flat optical matter, nor solely to transparent optical matter. Instead, the term is used to refer to an optical element that may or may not effect light passing there-through, but will permit at least a substantial portion of the light incident on the side of the window proximal to the light path 132 to exit the probe assembly 102 in a manner that is dependent on the properties of the optical element. In an embodiment, the optical window 203 may be transparent, which permits transmission of light, and specifically light emitted from the end of the light path 132, to volume 160 when the distal end of the probe 102 is in contact with or close proximity to that volume 160. In an embodiment, the optical window 203 may be translucent, permitting diffusion and transmission of light, and specifically light emitted from the end of the light path 132, to volume 160 when the distal end of the probe 102 is in contact with or close proximity to that volume 160. In an embodiment, the optical window 203 may be a lens, permitting the shaping and directing of light, and specifically light emitted from the end of the light path 132, to volume 160 when the distal end of the probe 102 is in contact with or close proximity to that volume 160.

In the assembled probe 102, one edge of the optical window 203 is in close proximity to, or in contact with, the transducer assembly 315. The proximity of the optical window 203 to the transducer assembly 315 allows light emitted from the optical window 203 to be emitted from a location close to the acoustic lens 205, and thus close to the plane of the transducer array 310.

In use, a coupling agent (e.g., gel) may be used to improve the acoustic contact between the distal end of probe 102 and the volume 160. If the coupling agent makes contact with the distal end of the optical fibers forming the light path 132, extraneous acoustic signal may be generated in response to light transmission over the light path 132. In an embodiment, the distal end of the probe 102, including optical window 203, mitigates the potential acoustic effect of a coupling agent in response to light emitting from the light path 132 by creating a gap between the coupling agent and the distal end of the optical fibers.

Figure 4:
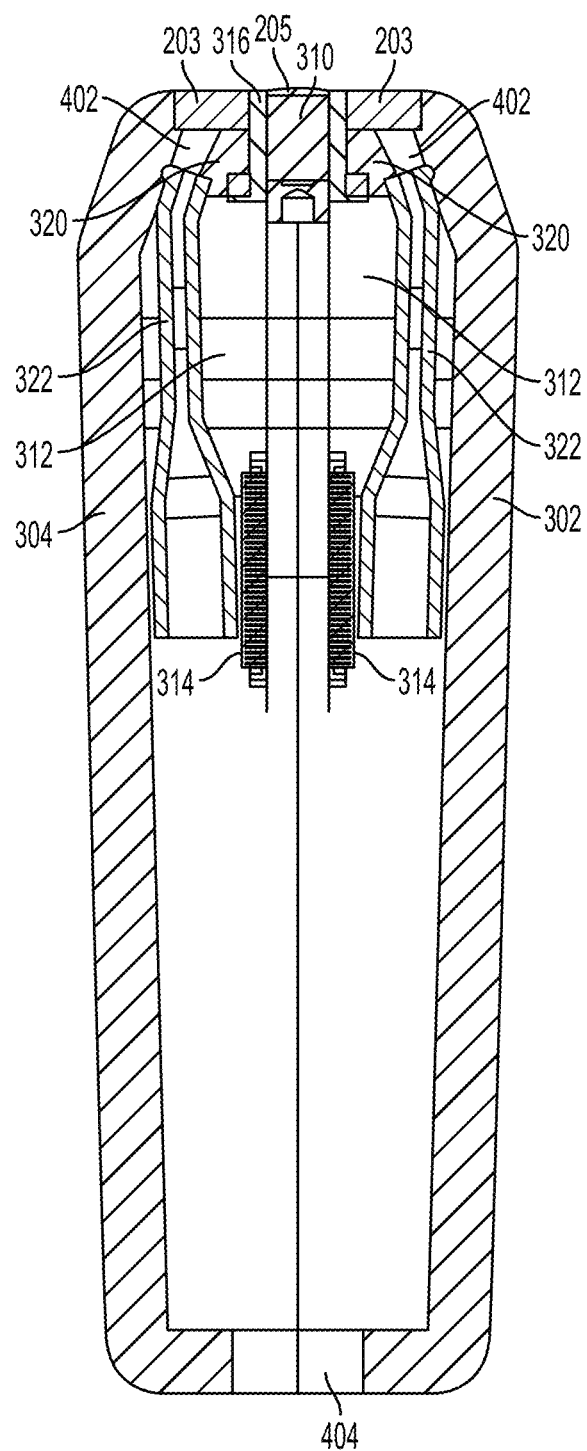
FIG. 4 shows a cutaway view taken along the centerline of the wider side of the probe shown in FIG. 2.

FIG. 4 shows a cutaway view taken along the centerline of the wider face of one embodiment of an assembled probe 102 such as the probe shown in FIG. 2. Shells 302, 304 support optical windows 203 and transducer assembly 315 at the distal end of the probe 102. Spacers 320 supported by transducer assembly 315 and shells 302, 304 aid in the positioning of optical windows 203 and light bar guides 322, and in maintaining gap 402 between light bar guides 322 and the optical windows 203.

The distal ends of the optical fibers making up the light path 132 may be positioned such that they do not create a physical sound conduction path to the volume 160 or to the acoustic transducers 310. In an embodiment, the gap 402 serves the purpose of preventing high frequency sound conduction path between the distal ends of the optical fibers making up the light path 132 and the volume 160 or the acoustic transducers 310. Specially selected materials, as discussed below, can be used to ensure that the light bar guide 322 reduces and/or minimizes the physical sound conduction path between the distal end of the light path 132 and the volume 160 or the acoustic transducers 310.

Flex circuit 312, with piezoelectric transducer elements (not shown) thereon, wraps around backing 311, and electrically connects the piezoelectric transducer elements with the cable connectors 314 at each end of the flex circuit.

Opening 404 in the shells 302, 304 provides an opening for optical path 132 (FIG. 1), electrical path 108 (FIG. 1) and optional power and control lines 109 (FIG. 1) to enter the inside of the probe 102. In an embodiment, a rubber grommet (not shown) may be used to provide stability and strain relief to the paths or lines passing into the probe 102 through opening 404.

Figure 5A:
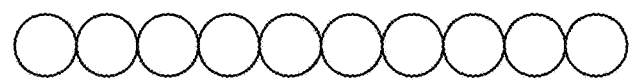
FIG. 5A is a side-view not-to-scale diagrammatic two dimensional representation of light exiting an optical fiber.
Figure 5B:
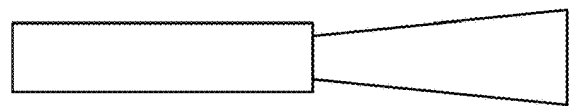
FIG. 5B shows an end view of a light pattern that may result on a surface from placement of optical fibers directly on to that surface.

Turning to FIG. 5A, a typical pattern of light striking a surface in close proximity to the ends of ten optical fibers is shown. Today, typical, reasonably flexible optical fibers have a diameter in the range of about 50 to 200 microns. Light exiting an optical fiber tends to expand slowly, see, for example, an illustrative example of light expanding after leaving the end of an optical fiber in FIG. 5B. The rate of expansion of the light beam leaving an optical fiber is a function of the diameter of the optical fiber and the refraction index of the optical fiber material. When a group of optical fibers are placed in close proximity to a surface to be illuminated, a light pattern like that seen in FIG. 5A results.

In an embodiment, optical fibers having smaller diameters are employed to broaden the illuminated area and minimize weight and increase flexibility of the light path 132. Light diverges as it exits a fiber optic, and its divergence as it exits is inversely related to the diameter of the fiber—in other words, light diverges faster out of smaller diameter fiber optics. Thus, for example, optical fibers in the range of under 50 microns, and potentially less than 30 microns may be desirable to broaden the illuminated area, thus reducing, or potentially eliminating the need for a beam expander. In an embodiment, the distal end of one or more groups of the optical fibers comprising the light path 132 may be fused to avoid the characteristic pattern of light shown in FIG. 5A.

In an embodiment, an optoacoustic probe should produce a relatively uniform light distribution incident upon the surface of the illuminated volume. It may also be desirable for an optoacoustic probe to produce a relatively large area of light distribution. Providing a relatively large and uniform light distribution permits an optoacoustic probe to deliver a maximum amount of energy without exceeding a specific light fluence on any given area of the illuminated surface, which can maximize patient safety and/or improve the signal-to-noise ratio. For these reasons, it is not desirable to locate the optical fiber ends in too close proximity with the surface of the illuminated volume, and thus, obtain a small or uneven light distribution such as the one seen in FIG. 5A.

In an embodiment, the optical fibers may be moved away from the surface of a volume to be illuminated. Moving the end of the optical fibers away from the surface of the volume to be illuminated will cause the beams emitted from each optical fiber to expand, and produce a more uniform area of light distribution. One potential issue associated with moving the optical fibers away from the surface of the volume to be illuminated, is the optoacoustic effects caused by stray portions of the expanding beam. Another potential issue is the effect of enlarging the distance (between the end of the optical fibers and the surface to be illuminated) on the shape or size of a probe. Further, increasing the number of optical fibers (and thus enlarging the area of the fiber bundle emitting light) will increase the cost, weight and flexibility of the optical path 132 (FIG. 1), and may also affect the size of the probe.

In an embodiment where the probe 102 is designed to be handheld, it is desirable to keep the probe head (the wider, distal portion of the probe 102) short so that the probe stem (the narrower, proximal portion of the probe 102) is relatively close to the surface of volume 160. Additionally, where a probe 102 is designed to be handheld, its total thickness is also a consideration for comfort, convenience and operational effectiveness. Accordingly, locating the distal ends of the fibers forming light path 132 at a sufficient distance from the optical window 203 to permit expansion to fill the optical windows 203 with uniform light fluence is not preferred. Similarly, using a very large number of fibers to enlarge the area of the fiber bundle held by the light bar guide 322 at the distal end of the light path 132 and thereby attempting to permit expansion to fill the optical windows 203 with uniform light fluence is also not preferred as it would, among other things cause undue weight, inflexibility, size and cost. Moreover, reducing the size of the optical window 203 would reduce the total potential safe energy output of the device, and thus, is not preferred.

Figure 6A:
FIG. 6A shows an end view of a desirable light pattern for use in connection with the optoacoustic techniques discussed herein.
Figure 6B:
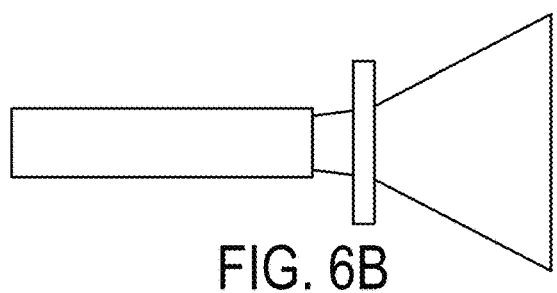
FIG. 6B shows a side view diagrammatic representation of an effect of a ground glass beam expander on the light emitting from a fiber shown in FIG. 5A.
Figure 6C:
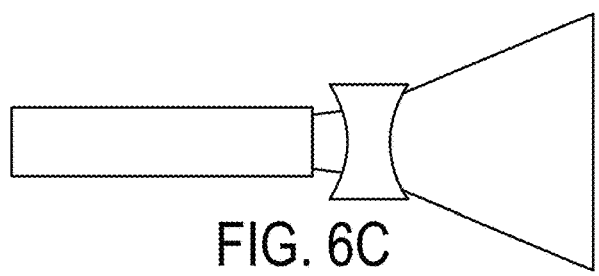
FIG. 6C shows a side view diagrammatic representation of an effect of a concave lens beam expander on the light emitting from a fiber shown in FIG. 5A.

Turning to FIGS. 6B and 6C, in an embodiment, a beam expander 601b, 601c may be used to expand the beam of light, causing it to become more uniform over a shorter distance. FIG. 6B shows the use of a ground or frosted glass beam expander 601b, while FIG. 6C shows the use of a lens beam expander 601c. In an embodiment, where the light bar guide 322 is generally rectangular, a lens beam expander 601c may be a cylindrical convex lens or a cylindrical concave lens. In an embodiment, a convex lens (not shown) may be used as a beam expander. It will be apparent to one of skill in the art that other lenses, lens systems or other optical systems or combinations thereof, can be used to spread and more evenly distribute the light.

Referring back to FIG. 4, in an embodiment, the light bar guides 322 are angled inward toward the ultrasonic imaging plane on the end retaining the distal ends of the fibers. The inward angling of the distal end of the light bar guide 322 permits the light emitting there-from to better fill, and thus, evenly illuminate the optical window 203. Gap 402, which may include a beam expander, may provide space for the light transmitted across the light path 132 to expand to fill the optical window 203. The inward angling tends to cause the direction of the light incident on the surface of the volume 160 to strike the surface at an angle less than normal, and thus, potentially, to better propagate into the volume beneath the acoustic lens 205 covering the ultrasound transducers 310.

Turning back to FIG. 1, because the probe 102 may be intended for handheld use, the weight and flexibility of the light path 132, the electrical path 108 and the optional power and control lines 109 is of consideration. In an embodiment, to make the light path 132 lighter and more flexible, the light path 132 is constructed from as few fibers as possible. A limiting factor to how few a number of fibers that can be used, is the amount of light carried across the optical path 132. The transmission of too much light over a fiber will damage the fiber. The light path 132 must carry the total amount of light that will be fluent on the surface of the volume 160, plus any light lost (e.g., absorbed or scattered) between the light source 129 and the surface of the volume 160 illuminated. Since the maximum area of illumination is known not to exceed the size of the optical window 203, and because the area of illumination is subject to fluence limits per unit area, a total light energy carried by the light path 132 can be approximated by multiplying the fluence limit by the size of the optical windows 203. The FDA provides numbers for the human safe level of fluence.

The volume 160 illuminated generally has its own optoacoustic response, which is especially apparent where light fluence is greatest, namely, at the surface of the volume 160. Increasing the area of illumination onto the surface of the volume 160 (e.g., by increasing the size of the optical window 203 and beam) reduces the optoacoustic affect generated by the surface of the volume 160 itself, and thus may reduce the undesirable optoacoustic signal generated by the surface of the volume 160 itself as compared to a desired signal representing the inhomogenities 161, 162.

In addition to unwanted optoacoustic signal generated by the surface of the volume 160 itself, there may be other sources of unwanted optoacoustic signals that can be detected by the ultrasound transducer, such as the side walls surrounding the space between the optical windows 205 and the respective light bar guides 322, the acoustic lens 205 and portions of the transducer housing 316. The optical windows 203 and any optional beam expander 601b, 601c may also be sources of unwanted optoacoustic signals that can be detected by the ultrasound transducer.

In an embodiment, the walls surrounding the space between the optical windows 205 and the respective light bar guides 322 may be made from a material that has high acoustic absorption properties and/or that is white and/or has high light scattering and/or reflecting properties. Using materials having these characteristics may reduce unwanted optoacoustic signals that can be detected by the ultrasound transducer. In an embodiment, the spacers 322 can be made from a resin material such as Micro-Mark CR-600, a two part high performance casting resin that dries to a white color.

In an embodiment, a layer (not shown) of material that has high acoustic absorption properties and/or that is white and/or has high light scattering properties is placed between the transducer assembly 315 and the light bar guides 322 in the assembled probe 102. Alternatively, the layer may be applied directly to the transducer assembly 315 or the light bar guide 322 where the two parts contact in the assembled probe 102. This layer may reduce unwanted optoacoustic signals that can be detected by the ultrasound transducer. In an embodiment, the layer can be made from a resin material such as Micro-Mark CR-600, a two part high performance casting resin that dries to a white color. In an embodiment, the layer (not shown) may also comprise a reflective coating. In an embodiment a reflective coating of gold is applied to the layer to reflect light that might otherwise strike the layer.

In an embodiment, anti-reflective coatings may be used to reduce the optoacoustic signature of the optical window 203 and/or the beam expander 601b, 601c. In an embodiment, magnesium fluoride may be used as an anti-reflective coating on the optical window 203 and/or the beam expander 601b, 601c. Anti-reflective coatings may be used to reduce and/or minimize energy absorbed or reflected by the optical window 203.

In an embodiment, the optoacoustic signature of the transducer assembly 315 and/or acoustic lens 205 can be reduced by whitening. In an embodiment, an acoustic lens 205 comprising RTV silicon rubber may be whitened and have its optoacoustic signature reduced by being doped with about 4% $TiO_2$. It is believed that the $TiO_2$ doping increases the reflectivity of the acoustic lens and therefore the absorption, and also has a scattering effect that tends to diffuse the optoacoustic response of the RTV silicon rubber, bringing the response down to a lower frequency which can be more easily filtered. As discussed above, the outer surface of the transducer assembly 315 and/or acoustic lens 205 may be given a metal coating, such as gold, copper, aluminum or brass. In an embodiment, the metal coating, and in particular, gold, reduces the optoacoustic signature of the transducer assembly 315 and/or acoustic lens 205. It is believed that gold reduces the optoacoustic signature of the acoustic lens 205 because of its high reflectivity in the light spectrum.

As discussed above, the optical fibers at the end of the optical path 132 are retained by the light bar guide 322 with all of the fiber ends retained by the light bar guide 322 located on substantially the same plane. In an embodiment, the fiber ends may be fixed in place using mechanical force, an adhesive, or a combination of mechanical force and an adhesive. The fibers may be glued near their distal end to keep them in the desired location and pattern, and/or to reduce output of mechanical energy due to laser firing. In an embodiment, the spaces between optical fibers fixed within the light bar guide 322 may be filled with a material having one or more of the following characteristics: sound absorbing, light scattering, white and/or light reflecting. In an embodiment, the optical fibers, which may be encased by a light bar guide 322 at the distal end of the light path 132 are fused. Fusing fibers at the distal end of the light path 132 may permit the light emitting from the light path to be more uniform.

In an embodiment, a reflective coating is placed on areas of the shells 302, 304 where laser light emanating from the optical path 132 may strike it, including with the assembled probe, and in the areas designed to make skin contact, e.g., near the optical window 203 and other portions of the distal end of the probe 102. In an embodiment, the shells 302, 304 are coated in gold where laser light emanating from the optical path 132 may, or is likely to strike it. In an embodiment, portions of the shell 302, 304 may be made from gold, although at present this may be cost prohibitive.

In an embodiment, a proximity detector system (not shown) is used to determine that the distal end of the probe 102 is on or very near the surface of a volume. Among the reasons such a proximity detector system is desirable is that it can be used to prevent pulsing of the light source 129 when the probe 102 is not in close proximity to a volume 160 under inspection, or to be inspected. This may be a safety issue as the light source 129 may produce light at levels that can be harmful, e.g., to the eyes. The proximity detector system may be implemented in the form of: a mechanical contact switch at the distal end of the probe; an optical switch looking at reflections of a non-harmful beam from the surface of the volume 160; a conductive switch that is closed by contact with the volume 160 and/or any acoustic gel or other materials between the volume 160 and the distal end of the probe; a conductive switch and a standoff comprising a conductive surface for contact with the distal end of the probe 102; a conductive switch and a thin, optically and acoustically transparent, conductive surface applied to the surface of the volume 160 of interest; an acoustic transducer switch that can detect close proximity of the volume 160 by transmitting and looking for the reflection of a sound within a specific time; an acoustic transducer switch that can detect close proximity of the volume 160 by using a narrow shape sound transmitter and receiver and using the reflection to detect proximity; using one or more of the transducers in the transducer array as a proximity detector by looking for a signal return; or by operating the device 100 in an ultrasound mode and looking for an ultrasound image.

In an embodiment, an optical detector (not shown) may be located in the probe 102 to take a measurement from which output energy can be estimated or deduced. In an embodiment, the optical detector will measure reflected energy such as energy reflected by the beam expander or optical window. In an embodiment, the optical detector will measure scattered energy such as energy scattered by the materials surrounding the gap 402. The measurement of the optical detector can be transmitted to the system chassis 101 via control signal line 109, where it can be analyzed to deduce or estimate the light output of the probe 102. In an embodiment, control functionality in the system chassis 101 can control or regulate the light output of the light system 129, and thus the light output of the probe 102 based on a measurement made by the optical detector. In an embodiment, control functionality in the system chassis 101 can control or regulate the gain in the transducer receivers to compensate for variation of the light output of the probe 102 based on a measurement made by the optical detector. In an embodiment, the computing subsystem 128 can trigger differing activity from light system 129 over control signal line 106 based on a measurement made by the optical detector. In an embodiment, a measurement made by the optical detector can be used to control for variations in the electrical system or the power to the device 101. Similarly, in an embodiment, a measurement made by the optical detector can be used to control for variations in the optical path 132 or other optical elements of the device 100. In an embodiment, the optical detector can be used to cause the fluence of light output by the probe 102 to remain close to, but below, safe limits by accommodating for variations in electrical or optical characteristics that might otherwise cause the fluence of light output by the probe 102 to exceed or fall far below the safe limit.

Figure 7:
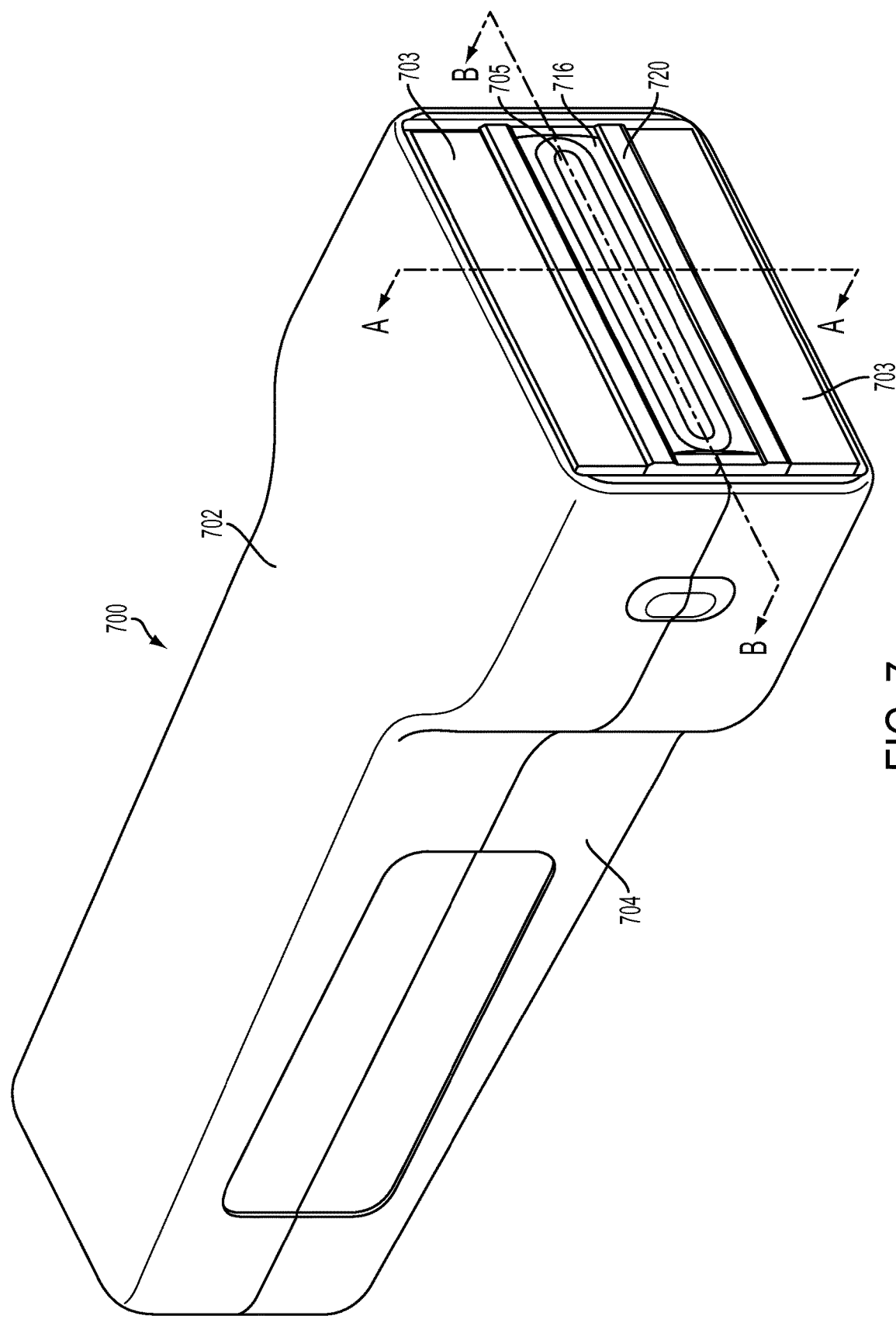
FIG. 7 shows a schematic orthogonal view of another embodiment of a probe that may be used in connection with the methods and other devices disclosed herein.
Figure 8:
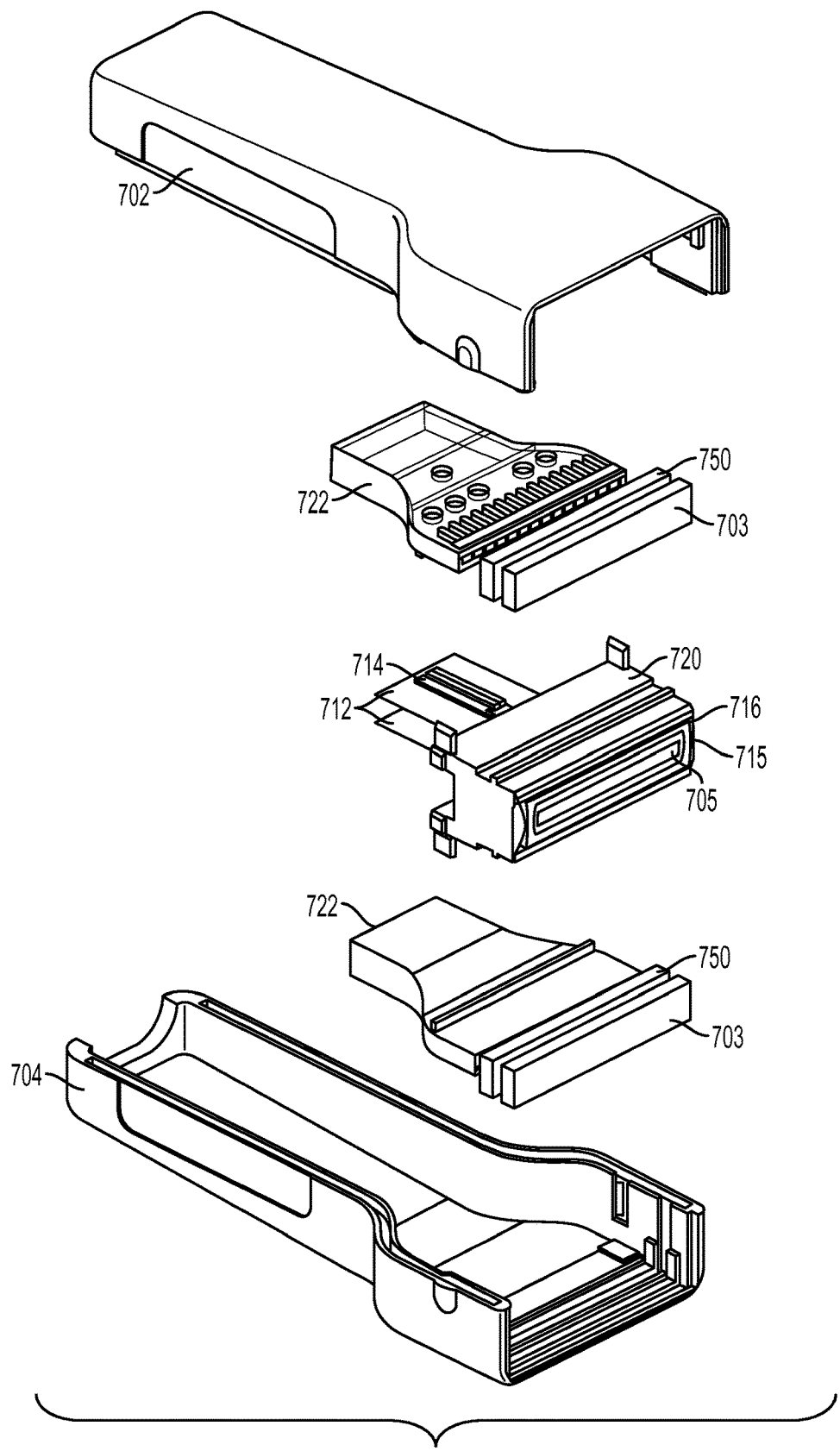
FIG. 8 shows an exploded orthogonal view of the embodiment of the probe shown in FIG. 7.
Figure 9:
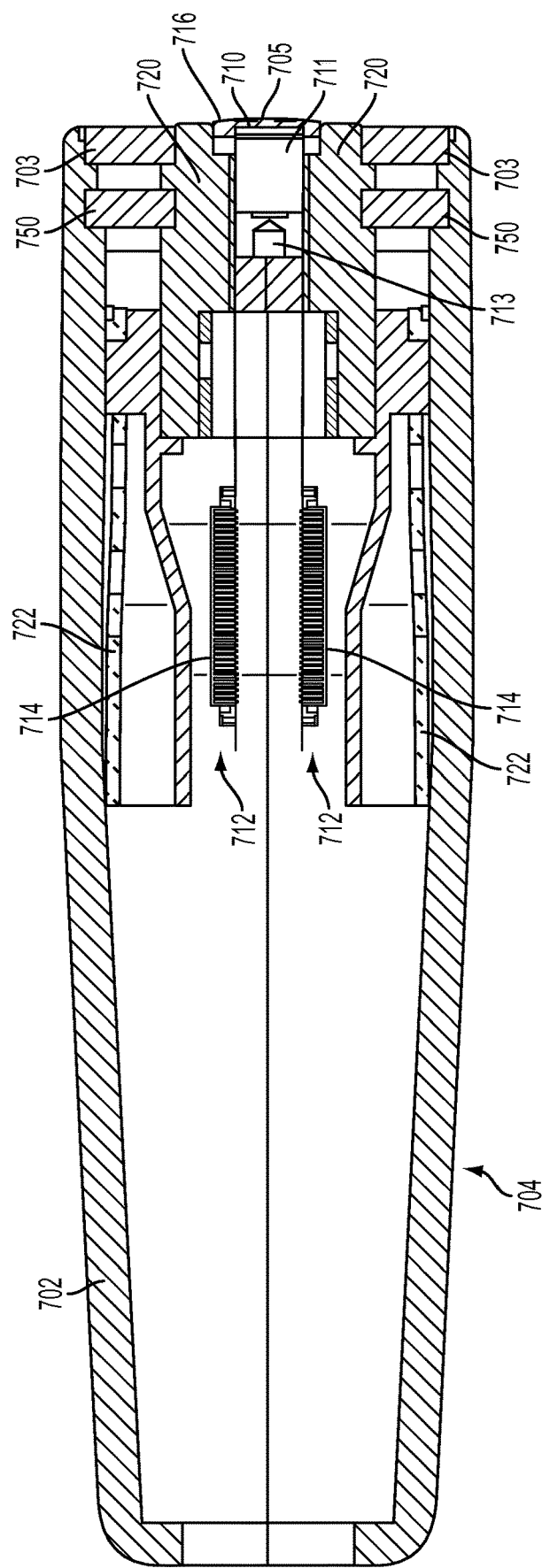
FIG. 9 shows a lengthwise cutaway view taken along line A-A of the probe shown in FIG. 7.
Figure 10:
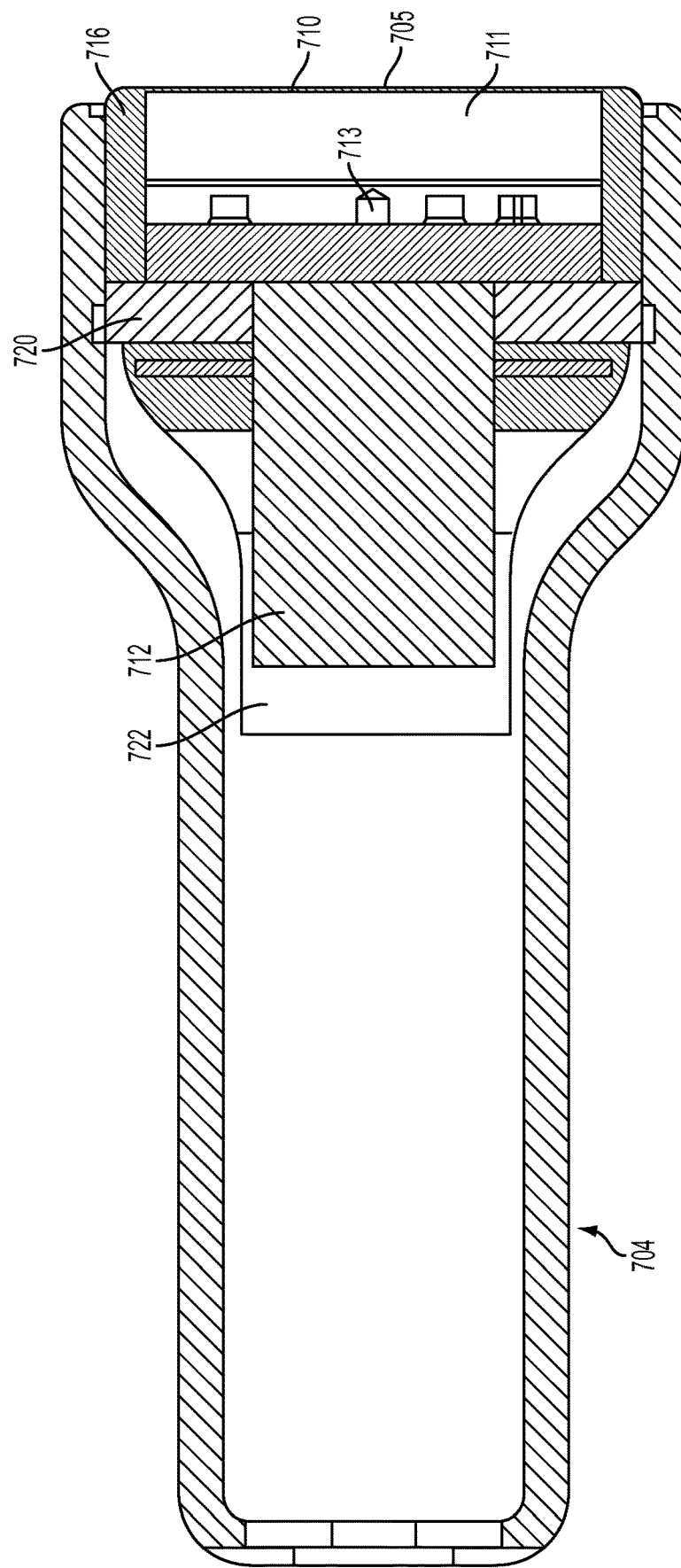
FIG. 10 shows a lengthwise cutaway view taken along line B-B of the probe shown in FIG. 7.
Figure 11:
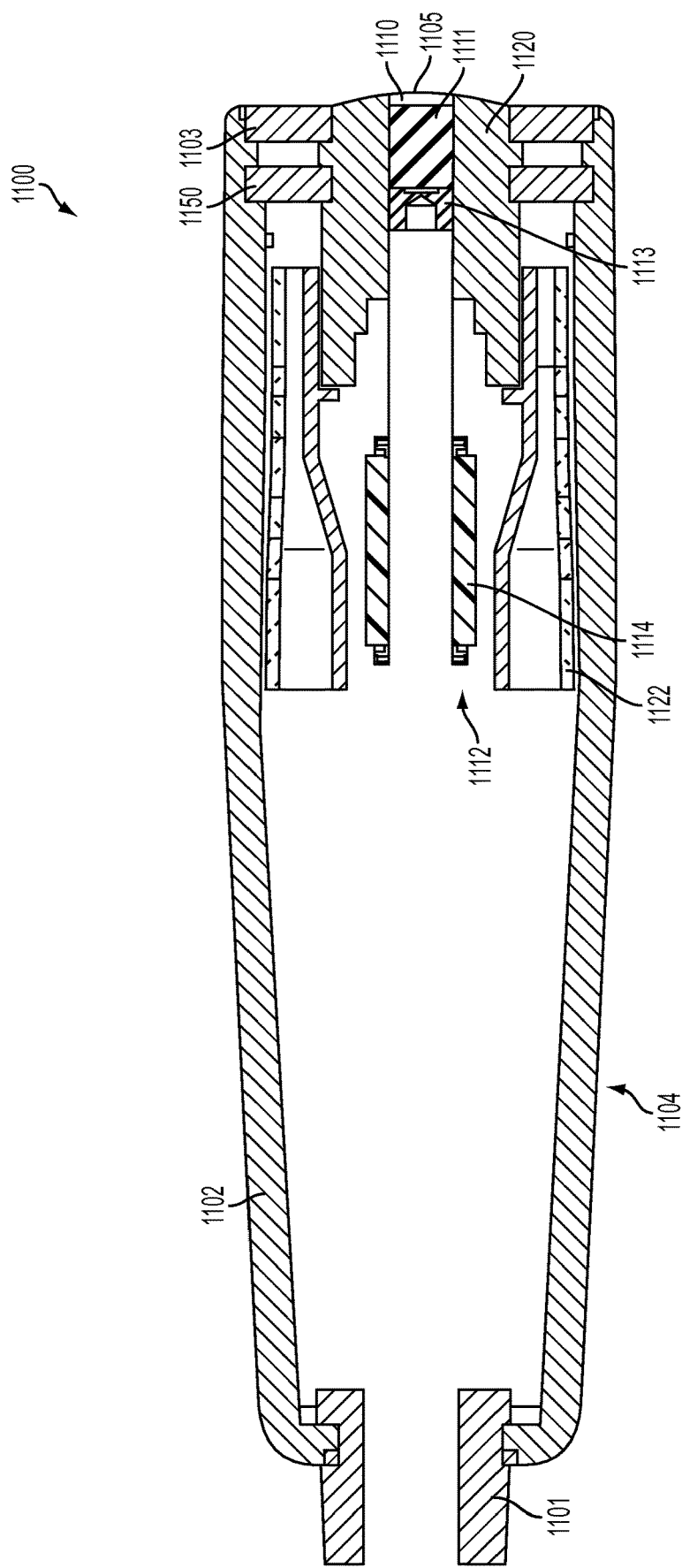
FIG. 11 shows a lengthwise cutaway view of another embodiment of a probe that may be used in connection with the methods and other devices disclosed herein.

FIG. 7 shows a schematic orthogonal view of another embodiment of a probe 700. FIG. 8 shows an exploded view of the probe 700, with the shells 702, 704 and other components separated to show the components of the probe 700 in more detail. FIGS. 9 and 10 show cutaway views of the probe 700 in its assembled state. FIG. 11 shows a lengthwise cutaway view of another embodiment of a probe that may be used in connection with the methods and other devices disclosed herein. As discussed below, several important differences exist between the probe 700 illustrated in FIGS. 7-10, and probe 1100 illustrated in FIG. 11 on the one hand, and the probe 102 shown in FIGS. 3 and 4 on the other, including, without limitation, physical separation of the window from the transducer assembly, shortening of the support housing for the acoustic lens, and importantly, use of an isolator instead of spacers.

As in the case of the probe shown in FIGS. 3 and 4, the shells 702, 704 may be made from plastic or any other suitable material. The surfaces of the shells 702, 704 that may be exposed to light, and especially light generated by the light subsystem 129, are preferably both reflective (i.e., light colored) material and light scattering (i.e., having a scattering coefficient between 1 and 10). In an embodiment, the surfaces of the shells 702, 704 are highly reflective, i.e., more than 75% reflective. In an embodiment, the surfaces of the shells 702, 704 are very highly reflective, i.e., more than about 90% reflective. In an embodiment, the surfaces of the shells 702, 704 have low optical absorption, i.e., less than 25% absorptive. In an embodiment, the surfaces of the shells 702, 704 have very low optical absorption, i.e., less than about 10% absorptive. In addition, the material forming the shells 702, 704 should be acoustically absorbent to absorb, rather than reflect or transmit acoustic energy. In an embodiment, white plastic shells 702, 704 are used.

As with flex circuit 312, in an embodiment, flex circuit 712 comprises a plurality of electrical traces (not shown) connecting cable connectors 714 to an array of piezoelectric ultrasound transducer elements (not shown) forming ultrasound transducer 710. In an embodiment, flex circuit 712 is folded and wrapped around a backing 711, and may be secured thereto using a bonding agent such as silicone. In an embodiment, a block 713 is affixed to the backing 711 opposite the array of piezoelectric ultrasound transducer elements. In an embodiment, the ultrasound transducer 710 comprises at least 128 transducer elements, although it may be desirable to have a greater numbers of transducer elements, as additional elements may reduce distortion, and/or increase resolution, accuracy and/or depth of imaging of the device 100. The cable connectors 714 operatively connect the electrical traces, and thus, the ultrasound transducer 710, to the electrical path 108. In an embodiment, the electrical path 108 may include a coaxial wire for each ultrasound transducer element in the ultrasound transducer array 710.

A surround 716 surrounds an acoustic lens 705, which is located in close proximity to, or in contact with the ultrasound transducer 710. As discussed above with respect to acoustic lens 205 and housing 216, the acoustic lens 705 and surround 716 may comprise a silicon rubber, such as a room temperature vulcanization (RTV) silicon rubber. In an embodiment, the surround 716 and the acoustic lens 205 may be formed as a single unit, from the same RTV silicon rubber material. In an embodiment, the ultrasound transducer 710 is secured behind the acoustic lens 705 using a suitable adhesive such as silicone. The transducer assembly 715, thus, may comprise the surround 716, acoustic lens 705, ultrasound transducer 710, the flex circuit 712 and its cable connectors 714, the backing 711, and block 713. In an embodiment, the backing 711 or block 713 can be used to affix or secure the transducer assembly 715 to other components.

Similar to the embodiment shown in FIGS. 3 and 4, to whiten, and reduce the optoacoustic effect of light generated by the light subsystem 129 on an RTV silicon rubber acoustic lens 705 and/or the surround 716, in an embodiment, the RTV silicon rubber forming the acoustic lens 705 and/or the surround 716 may be doped with TiO2. And, similar to the embodiment shown in FIGS. 3 and 4, in an embodiment, the RTV silicon rubber forming the acoustic lens 705 and/or the surround 716 may be doped with approximately 4% TiO2. In an embodiment, the outer surface of the acoustic lens 705 and/or the outer surface of the surround 716 may additionally be, or alternatively be, coated with a thin layer of metal such as brass, aluminum, copper or gold. In an embodiment, the outer surface of the acoustic lens 705 and/or the outer surface of the surround 716 may first coated with parylene, then coated with nickel, then coated with gold, and finally, again, coated with parylene. In an embodiment, the portions of the acoustic lens 705 and/or surround 716 having a perylene coating edge are adapted to be mechanically secured against other components to prevent curling or peeling. In an embodiment, substantially the entire outer surface of the surround 716, including the acoustic lens 705, are coated with continuous layers of parylene, then nickel, then gold and then parylene again. In an embodiment, substantially the entire outer surface of the surround 716 (including the acoustic lens 705), as well as the sides and underside of the surround 716, (but not the underside of the acoustic lens 705) may be coated with a continuous layer as described.

As with the embodiment shown in FIGS. 3 and 4, portions of the transducer assembly 715 behind the surround 716 may be surrounded, at least in part, by a reflective material, which may also serve as an electromagnetic shield.

In a substantial departure from the design of probe 102, however, isolators 720 in the probe 700 assembly physically separate the transducer assembly 715 from other probe components, including optical windows 703 and light bar guides 722, and in an embodiment, diffusers 750. Moreover, in an embodiment, the acoustic lens 705 and surround 716 are arranged in such a manner as to be the distal-most component of the probe 700, with the isolator 720 being next-distal-most, and the window 703 (if any) being proximal thereto. In an embodiment, the isolator 720 is arranged in such a manner as to be the distal-most component of the probe 700, with the outermost convex portion of the acoustic lens 705 being next-distal-most. In an embodiment (as shown in FIG. 9), the outermost convex portion of the acoustic lens 705 is arranged in such a manner as to be the distal-most component of the probe 700, with the isolator 720 being next-distal-most, and the window 703 (if any) and surround 716, being proximal to both the outermost portion of the acoustic lens 705 and the isolator 720. This latter orientation may better mitigate the propagation of acoustic/mechanical energy between the acoustic lens and the optical window 703 or other location where the light exits the probe toward the tissue of interest.

In an embodiment, isolators 720 are formed in a manner to aid in location and/or securing of optical windows 703, diffusers 750 and/or the surround 716. In an embodiment, isolators 720 comprise ridges or detents for to aid in location and/or securing of optical windows 703, diffusers 750 and/or the surround 716. In an embodiment, diffusers 750 may be holographic diffusers rather than a lens or ground or frosted glass beam expanders as discussed above.

As with spacers 320, the isolators 720 are made from materials that reduce the optoacoustic response to light generated by the light subsystem 129 which is ultimately transmitted to the transducer 710 during sampling. In an embodiment such as shown in FIGS. 3 and 4, the spacers 320 are whitened to reflect light generated by the light subsystem 129, thereby reducing the optoacoustic response of the spacers 320, thus mitigating the potentially interfering mechanical energy from transmission to the transducer during sampling. In a dramatic and non-obvious departure from that approach, in an embodiment, the isolators 720 are designed to absorb light generated by the light subsystem 129 rather than reflect it. In an embodiment, the isolators 720 are fabricated from a material that absorbs light and substantially prevents light from reaching the transducer assembly 715, but also dampens transmission of acoustic (e.g., mechanical) response to the light it has absorbed as well as the acoustic energy of surrounding components. In an embodiment, the isolators 720 are positioned so as to be substantially in the path of mechanical energy—such as any optoacoustic response, that originates with other components (e.g., the windows 703, or the diffusers 750)—that may reach the transducers 710 during an acoustic sampling process. In an embodiment, when assembled, the isolator 720 surrounds at least a substantial portion of the acoustic transducer assembly 715. In an embodiment, when assembled, the isolator 720 completely surrounds the acoustic transducer assembly 715. By surrounding the transducer assembly 715 with the isolators 720 and fabricating the isolators 720 from materials having the foregoing characteristics, the amount of mechanical or acoustic energy reaching the transducer 710 during sampling is mitigated.

The space between the isolator 720 on the one hand, and the flex circuit 712 and backing 711, on the other hand, is for illustrative purposes. In an embodiment, the isolator 720 is fabricated to fit snugly against the flex circuit 712 when it is assembled, for example, from two component parts. In such an embodiment, a thin layer of glue or other adhesive may be used to secure the isolator 720 in relation to the flex circuit 712, and thus, in relation to the transducer assembly 715. In an embodiment, the fit is not snug, and a gap between the isolator 720 and the flex circuit 712, and/or the backing 711 is filled, at least partially, with a glue or adhesive.

In an embodiment, the isolators 720 are fabricated from materials that will absorb that energy. In an embodiment, the material used to fabricate the isolator 720 is a compound made from silicone rubber, carbon black and microspheres.

FIG. 11 shows a lengthwise cutaway view of another embodiment of a probe 1100. The shells 1102, 1104 may be made from plastic or any other suitable material. The surfaces of the shells 1102, 1104 that may be exposed to light may be reflective or highly reflective and have low or very low optical and acoustic absorption. In an embodiment, flex circuit 1112 comprises a plurality of electrical traces (not shown) connecting cable connectors 1114 to an array of piezoelectric ultrasound transducer elements (not shown) forming ultrasound transducer 1110. In an embodiment, flex circuit 1112 is folded and wrapped around a backing 1111, and may be secured thereto using a bonding agent such as silicone. In an embodiment, a block 1113 is affixed to the backing 1111 opposite the array of piezoelectric ultrasound transducer elements. The cable connectors 1114 operatively connect the electrical traces, and thus, the ultrasound transducer 1110, to the electrical path 108. In an embodiment, the light path 132 and electrical path 108 are be run through strain relief 1101.

An acoustic lens 1105 is located in close proximity to, or in contact with the ultrasound transducer 1110. The acoustic lens 1105 may comprise a silicon rubber, such as a room temperature vulcanization (RTV) silicon rubber. In an embodiment, the ultrasound transducer 1110 is secured behind the acoustic lens 1105 using a suitable adhesive such as silicone. The transducer assembly, thus, may comprise the acoustic lens 1105, ultrasound transducer 1110, the flex circuit 1112 and its cable connectors 1114, the backing 1111, and block 1113. In an embodiment, the backing 1111 or block 1113 can be used to affix or secure the transducer assembly to other components.

In an embodiment, the RTV silicon rubber forming the acoustic lens 1105 may be doped with TiO2. In an embodiment, the RTV silicon rubber forming the acoustic lens 1105 may be doped with approximately 4% TiO2. In an embodiment, the outer surface of the acoustic lens 1105 may additionally be, or alternatively be, coated with a thin layer of metal such as brass, aluminum, copper or gold. In an embodiment, the outer surface of the acoustic lens 1105 may first coated with perylene, then coated with nickel, then coated with gold, and finally, again, coated with perylene. In an embodiment, the portions of the acoustic lens 1105 having a perylene coating edge are adapted to be mechanically secured against other components to prevent curling or peeling. In an embodiment, substantially the entire outer surface of the acoustic lens 1105, is coated with continuous layers of perylene, then nickel, then gold and then perylene again. In an embodiment, substantially the entire outer surface of the acoustic lens 1105 (but not its underside) may be coated with a continuous layer as described. Portions of the transducer assembly behind the acoustic lens 1105 may be surrounded, at least in part, by a reflective material, which may also serve as an electromagnetic shield.

Isolators 1120 physically separate the transducer assembly from other probe components, including optical windows 1103 and light bar guides 1122, and in an embodiment, diffusers 1150, which may be, among other choices, holographic diffusers or ground or frosted glass beam expanders. In an embodiment, isolators 1120 are formed in a manner to aid in location and/or securing of optical windows 1103, diffusers 1150 and/or the acoustic lens 1105. In an embodiment, isolators 1120 comprise ridges or detents for to aid in location and/or securing of optical windows 1103, diffusers 1150 and/or the lens 1105.

The isolators 1120 are made from materials that reduce the optoacoustic response to light generated by the light subsystem 129 which is ultimately transmitted to the transducer 1110 during sampling. In an embodiment, the isolators 1120 are fabricated from a material that absorbs light and substantially prevents light from reaching the transducer assembly, but also dampens transmission of acoustic (e.g., mechanical) response to the light it has absorbed as well as the acoustic energy of surrounding components. In an embodiment, the isolators 1120 are positioned so as to be substantially in the path of mechanical energy—such as any optoacoustic response, that originates with other components (e.g., the windows 1103, or the diffusers 1150)—that may reach the transducers 1110 during an acoustic sampling process. In an embodiment, when assembled, the isolator 1120 surrounds at least a substantial portion of the acoustic transducer assembly. In an embodiment, when assembled, the isolator 1120 completely surrounds the acoustic transducer assembly. By surrounding the transducer assembly with the isolators 1120 and fabricating the isolators 1120 from materials having the foregoing characteristics, the amount of mechanical or acoustic energy reaching the transducer 1110 during sampling is mitigated.

In an embodiment, the isolator 1120 is fabricated to fit snugly against the flex circuit 1112 when it is assembled. In an embodiment, a thin layer of glue or other adhesive may be used to secure the isolator 1120 in relation to the flex circuit 1112, and thus, in relation to the transducer assembly. In an embodiment, the fit is not snug, and a gap between the isolator 1120 and the flex circuit 1112, and/or the backing

1111 is filled, at least partially, with a glue or adhesive. In an embodiment, the isolators 1120 are fabricated from materials that will absorb that energy. In an embodiment, the material used to fabricate the isolator 1120 is a compound made from silicone rubber, carbon black and microspheres.

Formulation

In an embodiment, an isolator 720 or 1120 is fabricated from three principal components, a flexible carrier, a coloring and microbubbles. As used herein, the term microbubbles includes microspheres, low density particles or air bubbles. In an embodiment, an isolator 720 or 1120 may be fabricated from components in the following proportions: 22 g flexible material as a carrier; at least a small amount of coloring, but not so much that it thickens past mix-ability; and from about 10% to 80% microspheres by volume. In an embodiment, an isolator 720 or 1120 may be fabricated from components in the following proportions: 22 g flexible material as a carrier; at least a small amount of coloring, but not so much that it thickens past mix-ability; and about 10% to 80% air by volume, the air occurring in small bubbles. In an embodiment, an isolator 720 or 1120 may be fabricated from components in the following proportions: 22 g flexible material as a carrier; at least a small amount of coloring, but not so much that it thickens past mix-ability; and about 10% to 80% low density material particles—as compared to the flexible carrier.

In an embodiment, an isolator 720 or 1120 is fabricated from the following components: 22 g flexible material; between about 1/16 tsp and 1 tsp of coloring; and from about 25% to 70% by volume microbubbles. In an embodiment, the isolator 720 or 1120 is fabricated from the following components: 22 g flexible material; about 1/4 tsp of coloring; and around 50% by volume microbubbles. Although several of the foregoing proportions are given using 22 g of flexible carrier, that number is only given as an illustration. What is important are the proportional ranges of the materials used, not that it is made in batches of a specific size.

In an embodiment, the microspheres may have shells made from phenolic, acrylic, glass, or any other material that will create gaseous bubbles in the mixture. In an embodiment, the microspheres are small individual hollow spheres. As used herein the term sphere (e.g., microsphere), is not intended to define a particular shape, e.g., a round shape, but rather, is used to describe a void or bubble—thus, a phenolic microsphere defines a phenolic shell surrounding a gaseous void which could be cubic, spherical or other shapes. In an embodiment, air bubbles or a low density particles may be used instead of, or in addition to, the microspheres as microbubbles. In an embodiment, the microspheres, low density particles or air bubbles may range in size from about 10 to about 250 microns. In an embodiment, the microspheres, low density particles or air bubbles may range in size from about 50 to about 100 microns. In an embodiment, the isolator 720 or 1120 is formed from two or more parts. In an embodiment, the isolator 720 or 1120 is formed in two substantially identical halves.

In an embodiment, the silicon rubber compound may be a two part silicon rubber compound that can cure at room temperature. The flexible carrier may be a silicone rubber compound, or other rubber compound such as a high temperature cured rubber compound. In an embodiment, the flexible material may be any plastic material that can be molded or otherwise formed into the desired shape after being compounded with microspheres, low density particles and/or air bubbles and color ingredients. The coloring may be carbon black, or any other suitable coloring, including ink or dye, that will impart a dark, light-absorbing characteristic to the mixed compound.

In an embodiment, the following steps can be used to fabricate the isolators 720 or 1120. A mold may be prepared by applying thereto a thin release layer, such as a petroleum jelly. The ingredients are carefully measured and mixed until a uniform consistency is reached. Note care should be exercised in mixing because excessive mixing speed may entrap air in the mixture. The mixture is then placed into a mold appropriately shaped to form the isolator 720 or 1120 (or parts thereof). In an embodiment, an instrument is used to work the mixture into the corners of the mold. The mold is closed and pressed, with excess permitted to exit through vent holes. The mixture is then permitted to cure. Once cured, the casted part may be removed from the mold and cleaned to remove excess material, as is common, with a razor blade or other instrument(s). The cleaned parts may be washed with soap and water and wiped with alcohol to remove grease and/or dirt.

In an embodiment, portions of the fabricated part are coated with a reflective or highly reflective material such as gold or brass powder. In an embodiment, reflective gold coating may be used. In an embodiment, to coat the part, acrylic can be added drop-wise to a small amount of gold, brass or other reflective material until a suitable gold paint is achieved. In an embodiment, any reflective paint, e.g., gold colored paint, may be used. In an embodiment, care should be taken to avoid coating the distal end of the isolators 720 or 1120 which may come in contact with human tissue. To avoid such coating, the end of the isolators 720 or 1120 may be taped, such as with Teflon tape. In an embodiment, gold paint is painted on the front and side of the isolators 720 or 1120, i.e., the sides that will contact the glass 703 or 1103, diffuser 750 or 1150 and other components, excluding the transducer assembly 715. In an embodiment, a portion of the outer surface of the isolator 720 or 1120 may be coated with a layer of gold paint.

In an embodiment, a pair of halves of isolators 720 or 1120 may be made using the following amounts of the following components:

20 g of Momentive RTV 630A silicone rubber base (P/N: 038141)
2 g of Momentive RTV 630B silicone rubber curing agent (P/N: 038141)
1/4 tsp of carbon black (Leco P/N: 502-196)
5 tsp. of 70 micron phenolic microspheres (Eastech P/N: PHENOSET BJO-0840)

Clean tools should be used to thoroughly mix the ingredients. Use of accurate proportions of the Momentive RTV is important to producing a good result. The mixture may be sufficiently cured for handling after leaving it overnight, or within 24 hours, but it may take as much as a week for the mixture to fully cure at or around room temperature. Elevating the temperatures will speed the curing process, and thus, for example, heating the mixture to between 40-50° C. may permit handling within several hours.

The present system and methods are described above with reference to block diagrams and operational illustrations of methods and devices comprising an optoacoustic probe. It is understood that each block of the block diagrams or operational illustrations, and combinations of blocks in the block diagrams or operational illustrations, may be implemented by means of analog or digital hardware and computer program instructions. These computer program instructions may be provided to a processor of a general purpose computer, special purpose computer, ASIC, or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

While the invention has been particularly shown and described with reference to a preferred embodiment thereof, it will be understood by those skilled in the art that various changes in form and details may be made therein without departing from the spirit and scope of the invention.

What is claimed is:

1. An optoacoustic probe having a distal end, the probe comprising:
    a light path including an optical window proximal to the distal end of the probe, the light path being adapted to permit a light source to direct light towards the distal end of the probe;
    an acoustic lens having an inner surface and an outer surface;
    an ultrasound transducer array having an active end, the ultrasound transducer array having the inner surface of the acoustic lens at its active end;
    an isolator positioned between the optical window and the ultrasound transducer array and extending from the distal end of the probe through the probe to mitigate energy from the light path from affecting the ultrasound transducer array, the isolator being made from a mixture comprising a flexible carrier, a coloring, and between 10% and 80% by volume microbubbles; and
    a surround that surrounds the acoustic lens, wherein a distal-most portion of the acoustic lens is arranged in such a manner as to be the distal-most element of the probe, with the isolator being next-distal-most, and the surround being proximal to both the outermost portion of the acoustic lens and the isolator.

2. The optoacoustic probe claimed in claim 1, wherein the microbubbles are glass microspheres.

3. The optoacoustic probe claimed in claim 1, wherein the microbubbles are in the range of between 10 and 250 microns in diameter.

4. The optoacoustic probe claimed in claim 1, wherein the microbubbles are a variety of diameters, with the smallest being larger than 10 microns.

5. The optoacoustic probe claimed in claim 1, wherein the microbubbles are a variety of diameters, with the largest being smaller than 250 microns.

6. The optoacoustic probe claimed in claim 1, wherein the mixture is formed using a coloring selected from the group consisting of carbon black, ink and dye.

7. The optoacoustic probe claimed in claim 1, wherein the microbubbles are phenolic microspheres.

8. The optoacoustic probe claimed in claim 7, wherein the microspheres are in the range of between 50 and 100 microns in diameter.

9. The optoacoustic probe claimed in claim 7, wherein the microspheres are 70 microns in diameter.

10. The optoacoustic probe claimed in claim 1, wherein the mixture is formed using a silicone rubber compound as the flexible carrier.

11. The optoacoustic probe claimed in claim 10, wherein the mixture is formed using a two part silicone rubber compound as the flexible carrier.

12. The optoacoustic probe claimed in claim 10, wherein the mixture is formed using carbon black as the coloring.

13. The optoacoustic probe claimed in claim 12, wherein the carbon black and silicon rubber compound is in the following range of proportions, 22 g silicon rubber compound: between $1/16$ tsp and 1 tsp of carbon black.

14. The optoacoustic probe claimed in claim 1, further comprising a reflective coating on at least a portion of an outer surface of the isolator.

15. The optoacoustic probe claimed in claim 14, further comprising a gold colored reflective coating on at least a portion of the surface of the isolator exposed to the light path.

16. The optoacoustic probe claimed in claim 14, where the at least a portion of an outer surface of the isolator is a portion of the outer surface of the isolator that is exposed to light transmitted on the light path.

17. An optoacoustic probe having a distal end, the probe comprising:
    a light path adapted to permit a light source to direct light towards the distal end of the probe;
    an optical window in the light path proximal to the distal end of the probe;
    an acoustic lens having an inner surface and an outer surface;
    an ultrasound transducer array having an active end, the ultrasound transducer array having the inner surface of the acoustic lens at its active end;
    an isolator positioned between the optical window and the ultrasound transducer array and extending from the distal end of the probe through the probe to mitigate the light from the light path from striking the ultrasound transducer array before exiting the distal end of the probe, the isolator being made from a mixture including a coloring selected from the group of carbon black, dye, ink, and white resin; and
    a surround that surrounds the acoustic lens, wherein a distal-most portion of the acoustic lens is arranged in such a manner as to be the distal-most element of the probe, with the isolator being next-distal-most, and the surround being proximal to both the outermost portion of the acoustic lens and the isolator.

18. The optoacoustic probe claimed in claim 17, further comprising a surround that surrounds the acoustic lens, wherein a distal-most portion of the acoustic lens is arranged in such a manner as to be the distal-most element of the probe, with the isolator being next-distal-most, and the optical window and surround, being proximal to both the outermost portion of the acoustic lens and the isolator.

19. The optoacoustic probe claimed in claim 17, wherein the isolator isolates the ultrasound transducer array from all of the optoacoustic response of the optical window.

20. The optoacoustic probe claimed in claim 19, further comprising a diffuser positioned in the light path proximal to the optical window, the isolator being further adapted to isolate the ultrasound transducer array from all of the optoacoustic response of the diffuser.

21. The optoacoustic probe claimed in claim 20, wherein the diffuser is a holographic diffuser.

* * * * *